(12) United States Patent
Shortkroff et al.

(10) Patent No.: US 11,648,102 B2
(45) Date of Patent: *May 16, 2023

(54) METHOD FOR USE OF A DOUBLE-STRUCTURED TISSUE IMPLANT FOR TREATMENT OF TISSUE

(71) Applicant: Ocugen, Inc., Malvern, PA (US)

(72) Inventors: Sonya Shortkroff, Braintree, MA (US); Laurence J. B. Tarrant, Easthampton, MA (US); Eric J. Roos, Grafton, MA (US); Robert Lane Smith, Palo Alto, CA (US); Hans P. I. Claesson, Wayland, MA (US)

(73) Assignee: Ocugen, Inc., Malvern, PA (US)

( * ) Notice: Subject to any disclaimer, the term of this patent is extended or adjusted under 35 U.S.C. 154(b) by 353 days.

This patent is subject to a terminal disclaimer.

(21) Appl. No.: 17/098,851

(22) Filed: Nov. 16, 2020

(65) Prior Publication Data
US 2021/0059805 A1 Mar. 4, 2021

Related U.S. Application Data

(63) Continuation of application No. 15/977,552, filed on May 11, 2018, now Pat. No. 10,842,610, which is a (Continued)

(51) Int. Cl.
*A61F 2/02* (2006.01)
*A61F 2/30* (2006.01)
(Continued)

(52) U.S. Cl.
CPC ............ *A61F 2/02* (2013.01); *A61F 2/30756* (2013.01); *A61L 27/24* (2013.01); *A61L 27/34* (2013.01); *A61L 27/3604* (2013.01); *A61L 27/44* (2013.01); *A61L 27/48* (2013.01); *A61L 27/54* (2013.01); *A61L 27/56* (2013.01); *C07K 14/78* (2013.01); *A61F 2002/30075* (2013.01); *A61F 2002/3092* (2013.01); *A61F 2002/30766* (2013.01); *A61F 2210/0061* (2013.01); *A61F 2210/0076* (2013.01);
(Continued)

(58) Field of Classification Search
CPC .......... A61L 27/44; A61L 27/54; A61L 27/56; A61L 27/58
See application file for complete search history.

(56) References Cited

U.S. PATENT DOCUMENTS 5,830,493 A * 11/1998 Yokota ................... A61L 27/56
  623/23.61
6,306,169 B1 * 10/2001 Lee ..................... A61L 27/3804
  623/16.11
(Continued)

*Primary Examiner* — Todd J Scherbel
(74) *Attorney, Agent, or Firm* — Don D. Cha; HDC Intellectual Property Law, LLP

(57) ABSTRACT

A method for use of a double-structured tissue implant or a secondary scaffold stand-alone implant for treatment of tissue defects. The double-structured tissue implant comprising a primary scaffold and a secondary scaffold consisting of a soluble collagen solution in combination with a non-ionic surfactant generated and positioned within the primary scaffold. A method of use of a stand-alone secondary scaffold implant or unit for treatment of tissue defects.

11 Claims, 15 Drawing Sheets

DSTI Implantation

Related U.S. Application Data continuation of application No. 14/834,951, filed on Aug. 25, 2015, now Pat. No. 9,993,326, which is a continuation of application No. 13/897,816, filed on May 20, 2013, now Pat. No. 9,149,562, which is a continuation of application No. 12/194,771, filed on Aug. 20, 2008, now abandoned, which is a continuation-in-part of application No. 11/982,268, filed on Oct. 31, 2007, now Pat. No. 8,070,827, which is a continuation-in-part of application No. 11/894,124, filed on Aug. 20, 2007, now Pat. No. 8,685,107.

(60) Provisional application No. 60/967,886, filed on Sep. 6, 2007, provisional application No. 60/958,401, filed on Jul. 3, 2007.

(51) Int. Cl.
*A61L 27/34* (2006.01)
*A61L 27/24* (2006.01)
*A61L 27/48* (2006.01)
*A61L 27/56* (2006.01)
*C07K 14/78* (2006.01)
*A61L 27/44* (2006.01)
*A61L 27/54* (2006.01)
*A61L 27/36* (2006.01)

(52) U.S. Cl.
CPC ............... *A61F 2310/00365* (2013.01); *A61F 2310/00389* (2013.01); *A61L 2420/06* (2013.01); *A61L 2430/06* (2013.01)

(56) References Cited

U.S. PATENT DOCUMENTS 8,070,827 B2 * 12/2011 Shortkroff ............... A61L 27/38
    623/23.72
10,842,610 B2 * 11/2020 Shortkroff ............... A61L 27/54

* cited by examiner

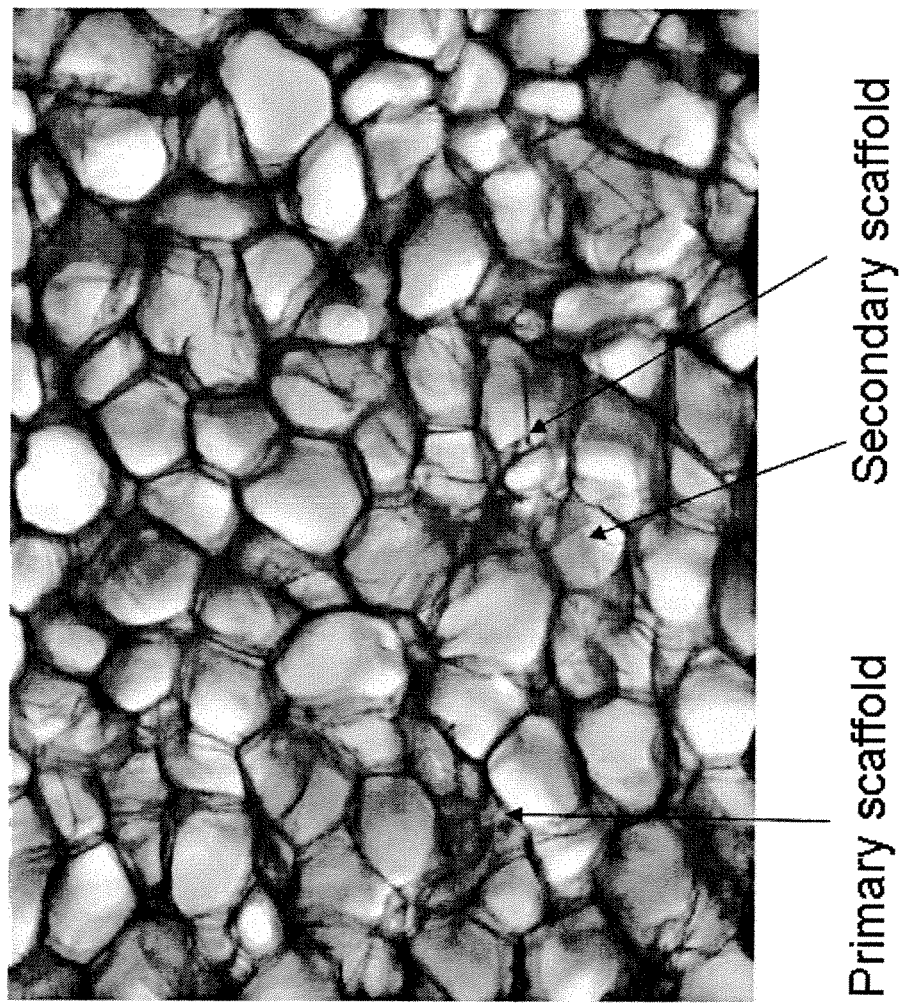

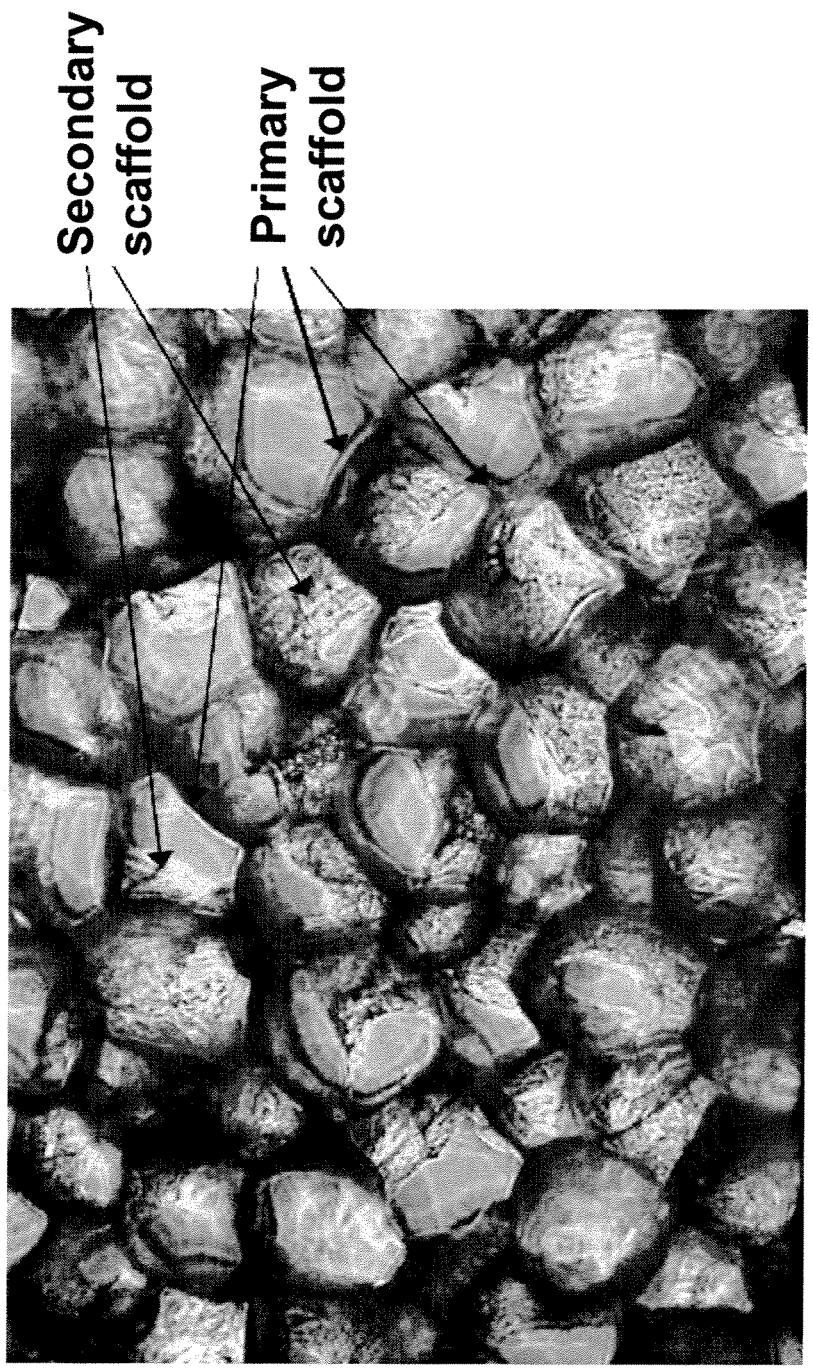

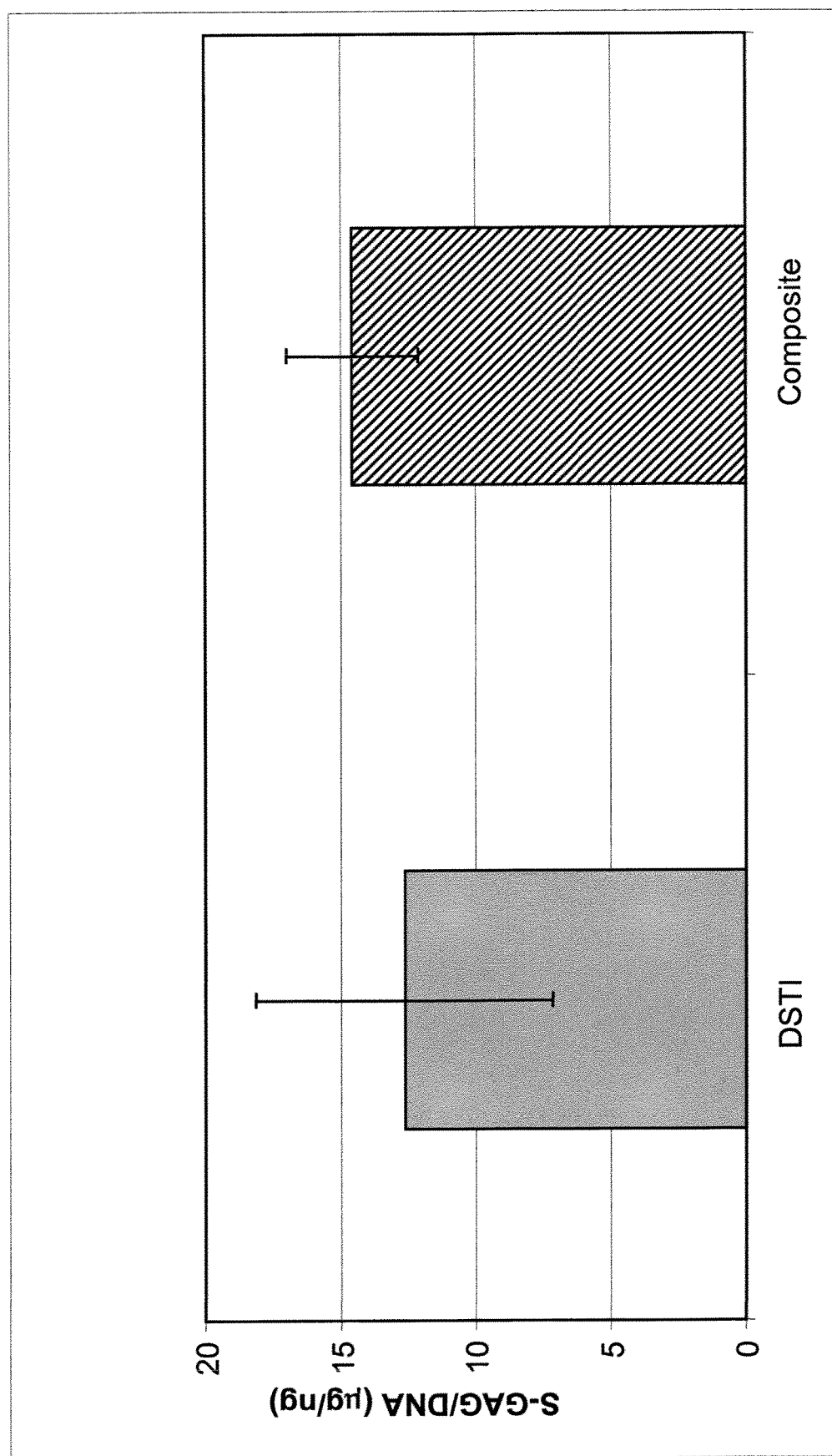

DSTI Implantation

DSTI Implantation

Fig. 9E
Implantation of DSTI Seeded/Cultured with Cells/Bone Marrow
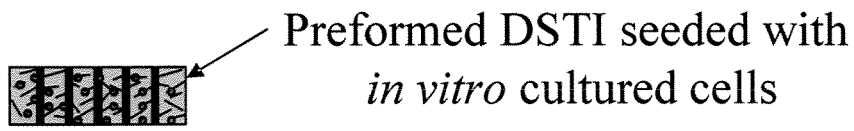 Preformed DSTI seeded with *in vitro* cultured cells
 Prepare Defect Site
Trim DSTI to Fill Defect Site
 Apply Adhesive to Defect Site
 Place DSTI in Defect Site
 Seal the Defect with Adhesive

METHOD FOR USE OF A DOUBLE-STRUCTURED TISSUE IMPLANT FOR TREATMENT OF TISSUE

This application is a continuation of U.S. patent application Ser. No. 15/977,552, filed May 11, 2018, which is a continuation of U.S. patent application Ser. No. 14/834,951, filed Aug. 25, 2015, now U.S. Pat. No. 9,993,326, which is a continuation of U.S. patent application Ser. No. 13/897,816, filed May 20, 2013, now U.S. Pat. No. 9,149,562, which is a continuation of U.S. patent application Ser. No. 12/194,771, filed Aug. 20, 2008, now abandoned, which is a continuation-in-part of U.S. patent application Ser. No. 11/982,268, filed Oct. 31, 2007, now U.S. Pat. No. 8,070,827, which is a continuation-in-part of U.S. patent application Ser. No. 11/894,124 filed on Aug. 20, 2007, now U.S. Pat. No. 8,685,107, and which claims benefit of U.S. Provisional Application Ser. No. 60/967,886, filed Sep. 6, 2007, and U.S. Provisional Application Ser. No. 60/958,401, filed Jul. 3, 2007, each of which is incorporated herein by reference in its entirety.

BACKGROUND OF THE INVENTION

Field of Invention

The current invention concerns a method for use of a double-structured tissue implant for implantation into tissue defects. In particular, the invention concerns use of a double-structured tissue implant comprising a primary scaffold and a secondary scaffold generated and positioned within the primary scaffold. The primary scaffold is a porous collagen-comprising material having randomly or non-randomly oriented pores of substantially homogeneous defined diameter. Under the most favorable conditions, the pores are through oriented, mostly vertically, and represent a high percentage of the total volume of the scaffold. The secondary scaffold is generated within the primary scaffold by introducing a composition comprising a soluble collagen solution in combination with a non-ionic surfactant into the pores of the primary scaffold and solidifying said composition within said pores using a novel process of the invention.

The method for use of the double-structured tissue implant comprises implantation of the DSTI into the tissue defect either in a rehydrated or dry form and sealing the implant within the defect with a biodegradable tissue sealant.

The DSTI may be rehydrated and/or preloaded with cells, drugs or growth modulators before or after implantation.

When formed, the double-structured tissue implant has improved properties, such as stability, resistance to shrinkage, swelling or dissolution, improved wetting, storageability and longer shelf-life as compared to the properties of each scaffold or the composite separately.

Furthermore, the double-structured tissue implant provides an increased surface area for cell adhesion, growth and differentiation without compromising the porosity of the implant.

Background and Related Disclosures

Collagen matrices for use as an implant for repair of cartilage defects and injuries are known in the art. Of a particular interest is a honeycomb structure developed by Koken Company, Ltd., Tokyo, Japan, under the trade name Honeycomb Sponge, described in the Japanese patent JP3170693, hereby incorporated by reference. Other patents related to the current subject disclose collagen-based substrates for tissue engineering (U.S. Pat. No. 6,790,454) collagen/polysaccharide bi-layer matrix (U.S. Pat. No. 6,773,723), collagen/polysaccharide bi-layer matrix (U.S. Pat. No. 6,896,904), matrix for tissue engineering formed of hyaluronic acid and hydrolyzed collagen (U.S. Pat. No. 6,737,072), method for making a porous matrix particle (U.S. Pat. No. 5,629,191) method for making porous biodegradable polymers (U.S. Pat. No. 6,673,286), process for growing tissue in a macroporous polymer scaffold (U.S. Pat. No. 6,875,442), method for preserving porosity in porous materials (U.S. Pat. No. 4,522,753), method for preparation of collagen-glycosaminoglycan composite materials (U.S. Pat. No. 4,448,718), procedures for preparing composite materials from collagen and glycosaminoglycan (U.S. Pat. No. 4,350,629) and a crosslinked collagen-mucopolysaccharide composite materials (U.S. Pat. No. 4,280,954).

However, many of the above disclosed structures have uncontrolled parameters such as uneven and uncontrolled porosity, uneven density of pores, uneven sizes of the pores and random distribution of pores within the support matrix. Such uncontrolled parameters lead to usable pore structures that represent only a small percentage of the total implant. Additionally, when introduced into tissue defects or cartilage lesions during the surgery, these structures are difficult to handle as they are unstable and do not have appropriate wetting properties in that they can shrink or swell and are not easily manipulated by the surgeon.

For a tissue implant to be suitable for implantation, particularly for implantation into the cartilage lesion, the implant needs to be stable, easily manipulated, easily stored in sterile form and have a long shelf-life.

In order to provide a more uniform and sterically stable support structure for implantation into a tissue defect or cartilage lesion, inventors previously developed a collagen matrix having narrowly defined size and density of pores wherein the pores are uniformly distributed, vertically oriented and non-randomly organized. This matrix is disclosed in the co-pending patent application Ser. No. 11/523,833, filed on Sep. 19, 2006, hereby incorporated by reference in its entirety. Additionally, the acellular matrix suitable to be used as the primary scaffold is described in the priority application Ser. No. 10/882,581, filed on Jun. 30, 2004, issued as U.S. Pat. No. 7,217,294, on May 15, 2007, hereby incorporated in its entirety. However, even with the above-described improvements, a solution to problems faced by the surgeon during surgery is still lacking. A practicality needed for routine use of the tissue implants, such as, for example, the articular cartilage implants by the orthopedic surgeons, where the implant needs to be readily available, manipulatable, wettable, stable, sterile and able to be rapidly prepared and used for implantation, is still not achieved. All the previously described and prepared matrices or scaffolds require multiple steps before they are fully implantable.

Thus, it would be advantageous to have available an implant that would be easily manufactured and packaged, would be stable for extended shelf-life, would be easily manipulatable and rapidly wettable upon introduction into the lesion, could provide a support for cell migration or seeding and that could have, additionally, pre-incorporated drug or modulator in at least one portion of the implant. The implant should also allow the surgeon to introduce a drug or modulator during the surgical procedure.

It would also be an advantage to provide a secondary scaffold with an increased area of internal membranes which while not interfering with cell migration and nutrient exchange, nevertheless, would provide a substrate favorable to cell adhesion, growth and migration.

It is, therefore, a primary object of this invention to provide a method for treatment of tissue defects using a double-structured tissue implant comprising a primary scaffold and a secondary scaffold where each scaffold of the implant can assume a different function, be incorporated with cells, different drugs or modulators and/or be selectively chosen for performing a different function following the implantation.

The current invention provides such double-structured scaffold and a method for use for treatment of tissue defects by providing a first scaffold comprising a sterically stable and biocompatible support structure, preferably made of collagen, having defined pore sizes and density with said pores organized vertically and a second scaffold wherein said second scaffold is formed within said pores of said first scaffold. The double-structured scaffold of the invention is stable, resistant to shrinkage, swelling and dissolution, rapidly wettable, prepared in the sterile storageable form having a long-shelf life that can be easily surgically delivered and easily manipulated.

All patents, patent applications and publications cited herein are hereby incorporated by reference.

SUMMARY

One aspect of the current invention is a method for use of a double-structured tissue implant for treatment of tissue defects.

Another aspect of the current invention is a collagen-based double-structured tissue implant comprising a primary scaffold and a secondary scaffold wherein said secondary scaffold is a qualitatively different structure formed within a confine of the primary scaffold wherein said implant is suitable for implantation into tissue lesions or defects.

Another aspect of the current invention is a collagen-based primary porous scaffold having randomly oriented open pores of substantially homogeneous pore size, said primary scaffold suitable for incorporation of a secondary scaffold wherein said secondary scaffold is incorporated into said primary scaffold by introducing a Basic Solution comprising collagen and a non-ionic surfactant into said primary scaffold and subjecting said primary scaffold incorporated with said Basic Solution for the secondary scaffold to a process comprising precipitation, lyophilization and dehydrothermal treatment.

Still yet another aspect of the current invention is a method of use for a double-structured tissue implant having two distinct qualitatively different structures wherein each of the structures may be independently loaded with cells or prepared already incorporated with drugs or growth modulators or wherein both structures of the implant may comprise cells, pharmaceutical agents or growth modulators.

Still another aspect of the current invention is a method of use for a double-structured tissue implant empty or seeded with cells or incorporated with drugs or growth modulators for implantation into tissue lesions or defects wherein said implant is placed into said lesion or defect and covered with an adhesive and wherein when the implant is seeded with cells or in vitro cultured cells, the sealant or adhesive is applied to both the bottom of the lesion and at the top of the lesion.

Still another aspect of the current invention is a method of use for a secondary scaffold as a stand alone implant or unit for tissue implantation, wherein said secondary scaffold is prepared from the Basic Solution comprising collagen and a surfactant neutralized to pH of about 7.4 and subjected to lyophilization and dehydrothermal treatment.

Yet another aspect of the current invention is a method for use of a double-structured tissue implant or the stand alone secondary scaffold implant for implantation into a tissue defect or cartilage lesion wherein said implant, in dry or wet form, optionally seeded with cells is implanted into said defect or lesion during surgery and covered with at least a top adhesive.

Another aspect of the current invention is a process for preparation of a double-structured implant by providing a primary porous scaffold prepared from a biocompatible collagen material wherein said scaffold has a substantially homogenous defined porosity and uniformly distributed randomly and non-randomly organized pores of substantially the same size of defined diameter of about 200 to 300±100 μm, wherein said primary scaffold is brought in contact with a soluble collagen based solution comprising at least one non-ionic surfactant (Basic Solution), wherein such solution is introduced into said pores of said primary scaffold, stabilized therein by precipitation or gelling, dehydrated, lyophilized and dehydrothermally processed to form a distinctly structurally and functionally different second scaffold within said pores of said primary scaffold.

BRIEF DESCRIPTION OF FIGURES

FIG. 4A is a photomicrograph of a rehydrated double-structured tissue implant (DSTI) showing a primary and secondary scaffold (4× magnification). FIG. 4A demonstrates the formation of the double-structured implant, where the secondary scaffold is observed from the fibrous-like diffraction pattern present within the pores of the primary scaffold. The diffraction pattern is created from the polymerization of the collagen within the pores.

The collagen fibers interdigitate within the pores and among the pores. FIG. 4B is a photomicrograph of the dehydrated double-structured tissue implant prior to implantation showing a primary and secondary scaffold (4× magnification). Similarly to FIG. 4A, FIG. 4B shows the double-structured implant wherein the secondary scaffold is seen as the fibrous-like diffraction pattern present within the pores of the primary scaffold.

FIG. 6 demonstrates the structural stability of the collagen network present in the double-structured implant (DSTI) as a function of time (in days) in an aqueous buffered saline solution. The data demonstrate that during the first day following the rehydration, there is very little dissolution of collagen from the DSTI and that the retention of collagen is close to 100% during the initial first critical hour in all three DSTIs (Lots 1-3). On the other hand, the dissolution from the Composite in the initial hour is much higher and retention decreases immediately to approximately 96% during that same critical first hour. FIG. 6 thus clearly demonstrates a stability of the DSTI.

FIG. 8 is a graph showing production of S-GAG/DNA by chondrocytes seeded in double-structured tissue implant (DSTI) and in a composite (Composite) comprising a primary scaffold loaded with a composition for a secondary scaffold before lyophilization and dehydrothermal processing, after 14 days in culture. FIG. 8 demonstrates that secondary scaffold supports the growth of cells and deposition of extracellular matrix measured here as sulfated glycosaminoglycan. A comparison between the double-structured tissue implant and the Composite showed comparable results with little evidence of significant steric hindrance due to the added structural components.

FIGS. 9A and 9B illustrate the implantation method in a surgical operating room setting. The defect site is prepared and an initially oversized double-structured tissue implant (DSTI) is cut and trimmed to match the size and shape of the defect. In FIG. 9B, subchondral plate of the defect site is penetrated using the microfracture technique. The precut DSTI is rehydrated with physiologically acceptable solution and placed into the defect. Alternatively, the dehydrated DSTI is implanted and rehydrated in situ. The DSTI is rehydrated with a physiologically acceptable solution optionally containing cells, cell progenitors or agents that stimulate healing. The defect site is sealed with a tissue adhesive applied over the implant. Optionally, the same or different adhesive is also applied to the defect site to coat the defect site (FIG. 9C) before the implant is placed. In case of a microfractured defect as seen in FIG. 9D, the adhesive is applied between microfracture penetrations.

DEFINITIONS

Figure 1A:
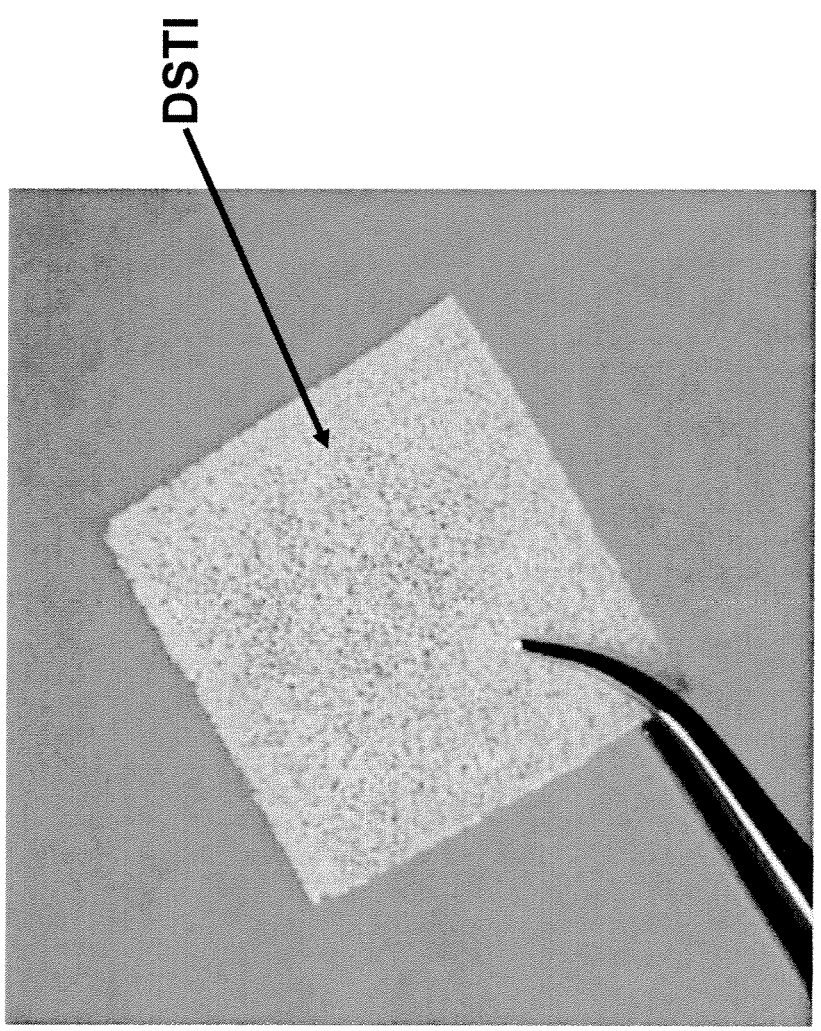
FIG. 1A is a photograph of the lyophilized double-structured tissue implant (DSTI) that shows the porous nature and the sturdiness of the implant prior to rehydration.

As used herein:

"Primary scaffold" means a porous honeycomb, sponge, lattice or another structure made of collagen or collagen based material having randomly or non-randomly oriented pores of substantially homogenous defined diameter. Under the most favorable conditions, the pores are vertically oriented and represent a high percentage of the porosity of the scaffold "Secondary scaffold" means a collagen based structured prepared from a collagen or collagen based compound and a non-ionic surfactant. The secondary scaffold is generated within the primary scaffold by introducing a composition comprising a soluble collagen solution in combination with a non-ionic surfactant (Basic Solution) into the pores of the primary scaffold and solidifying said composition within said pores using a process of the invention.

"Basic Solution" means a solution comprising a collagen in admixture with a surfactant, preferably PLURONIC®-type surfactant, neutralized to the pH of about 7.4. Basic Solution is used for preparation of the secondary scaffold.

"Composite" means a primary scaffold loaded with a composition comprising a precipitated or gelled soluble collagen in combination with a non-ionic surfactant (Basic Solution). The composite is in a hydrated form because the Basic Solution is added in a fluid form as a gel, suspension or solution.

"Lyophilized composite" means the hydrated "composite", as defined above, that is subsequently subjected to a dehydration and lyophilization step.

"Double-structured tissue implant" or "DSTI" means a tissue implant prepared according to a process of the invention wherein the primary scaffold is loaded with a Basic Solution thereby forming a composite that is subsequently subjected to precipitation, dehydration and lyophilization to obtain lyophilized composite that is subsequently treated with dehydrothermal (DHT) treatment to result in a stable double-structured tissue implant.

"Surfactant" means a non-ionic or ionic surfactant polymer. Suitable surfactants, such as PLURONIC®-type polymers or TRITON®-type polymers, are non-ionic co-polymer surfactants consisting of polyethylene and polypropylene oxide blocks. TRITON®-type surfactants are commercially available derivatized polyethylene oxides, such as for example, polyethylene oxide p-(1,1,3,3-tetramethylbutyl)-phenyl ether, known under its trade name as TRITON®-X100. Other TRITON®-type surfactants that may be suitable for use in the instant invention are TRITON® X-15, TRITON® X-35, TRITON® X-45, TRITON® X-114 and TRITON® X-102. TRITON® surfactants are commercially available from, for example, Union Carbide, Inc. PLURONIC®-type surfactants are commercially available block co-polymers of polyoxyethylene (PEO) and polyoxypropylene (PPO) having the following generic organization of polymeric blocks: PEO-PPO-PEO (Pluronic) or PPO-PEO-PPO (Pluronic R). Exemplary PLURONIC®- type surfactants are PLURONIC® F68, PLURONIC® F127, PLURONIC® F108, PLURONIC® F98, PLURONIC® F88, PLURONIC® F87, PLURONIC® F77, PLURONIC® F68, PLURONIC® 17R8 and PLURONIC® 10R8.

"The porosity" means a pore size defined by the diameter of holes within the primary scaffold as well as density of the pore distribution as a function of cross-sectional area in millimeters. Porosity is defined as a total volume of pores relative to the implant.

"Substantially homogeneous" means at least 85-99% homogeneity. Preferable homogeneity is between 95% and 99%.

"Substantially homogeneous porosity" means that a pore size and diameter is within pore size range of about 200 to 300±100 cm, preferably 300±50 cm, in diameter.

"Wettability" means an ability to quickly absorb a fluid into the DSTI without changes in the size and shape of the implant.

"Shrinkage" means a volumetric reduction in surface area in all dimensions of a double structured tissue implant.

"Swelling" means a volumetric increase of a surface area in all dimensions of a double structured tissue implant.

"Dissolution" means the act of a solid matter being solubilized by a solvent.

"Rehydration" means the act of hydrating, wetting or rewetting a dehydrated composite, lyophilized composite, stand alone secondary scaffold or double structured tissue implant. Rehydration may be performed before the implantation or after the implantation of the DSTI into the tissue defect. Rehydration utilizes a medium or fluid consisting of physiological fluid alone or mixed with cells, stem cells, bone marrow aspirate, bone marrow stem cells, drugs, or growth modulators.

"Dehydrothermal treatment" means removing water at low pressure and at high temperature for cross-linking of polymers.

"Top surface" means an apical or synovial side of the matrix turned toward the joint.

"Bottom surface" means basal, closest to bone surface of the matrix.

"Cell" or "cells" means chondrocytes, synovial cells, tendon cells, ligament cells, bone cells, mesenchymal stem cells, embryonic stem cells, satellite cells, progenitor cells, cell lines, virally transfected cell lines and any other cells that have capability to form a differentiated tissue, such as, for example, connective muscle or endothelial tissue.

"Tissue" means cartilage, ligament, tendon, bone, connective tissue, nervous tissue, muscle, heart tissue, endothelial or spinal cord tissue.

"Chondrocytes" means the cells naturally residing in articular cartilage.

"S-GAG" means sulfated glycosaminoglycan.

Substantially" means at least 70%.

DETAILED DESCRIPTION OF THE INVENTION

The current invention is directed to a method of use of a double-structured tissue implant suitable for implantation into tissue defects and lesions in a clinical setting for repair of tissue lesions. The double-structured implant has improved properties compared to a single structured implant and provides for variability in use. The double-structured tissue implant (DSTI) comprises a primary collagen-based structure, hereinafter called a primary scaffold, and a secondary collagen-based structure, hereinafter called a secondary scaffold. The two scaffolds are structurally and functionally different. Each scaffold is prepared from a different collagen-based composition with the primary scaffold prepared first and the secondary scaffold prepared by introducing a different collagen-based composition within the primary scaffold thereby forming a composite structure comprising the primary scaffold incorporated with a solution comprising a collagen in admixture with a surfactant (Basic Solution) for preparation of said secondary scaffold. The composite structure (Composite) is then subjected to a lyophilization and dehydrothermal treatment process according to the invention.

The resulting double-structured tissue implant (DSTI) thus contains a structurally different secondary scaffold incorporated into and localized within pores of the primary scaffold.

The actual photograph of a double-structured tissue implant provided to a surgeon is seen in FIG. 1 in two manifestations.

FIG. 1A shows a close-up view of a DSTI, as delivered to the surgeon in ready form for implantation. Before implanting, the surgeon cuts the piece of the implant and trims it to a size and shape corresponding to the size and shape of the defect or lesion, places the precut section into the defect and rehydrates the implant with sterile phosphate buffered saline or another physiologically acceptable solution optionally containing cells, such as chondrocytes, fibroblasts, mesenchymal stem cells, bone marrow aspirate, bone marrow stem cells or any other cells, cell suspensions or solutions containing growth hormone, mediators, drugs, etc., as appropriate. Alternatively, such rehydration may be performed before implanting said implant into the defect. The precut implant is suitable for placement within a full thickness defect of a tissue, and particularly for placement into an articular cartilage lesion. Once in place, the double-structured tissue implant can be held in place by suture, biologically acceptable adhesive or a combination of both.

Figure 1B:
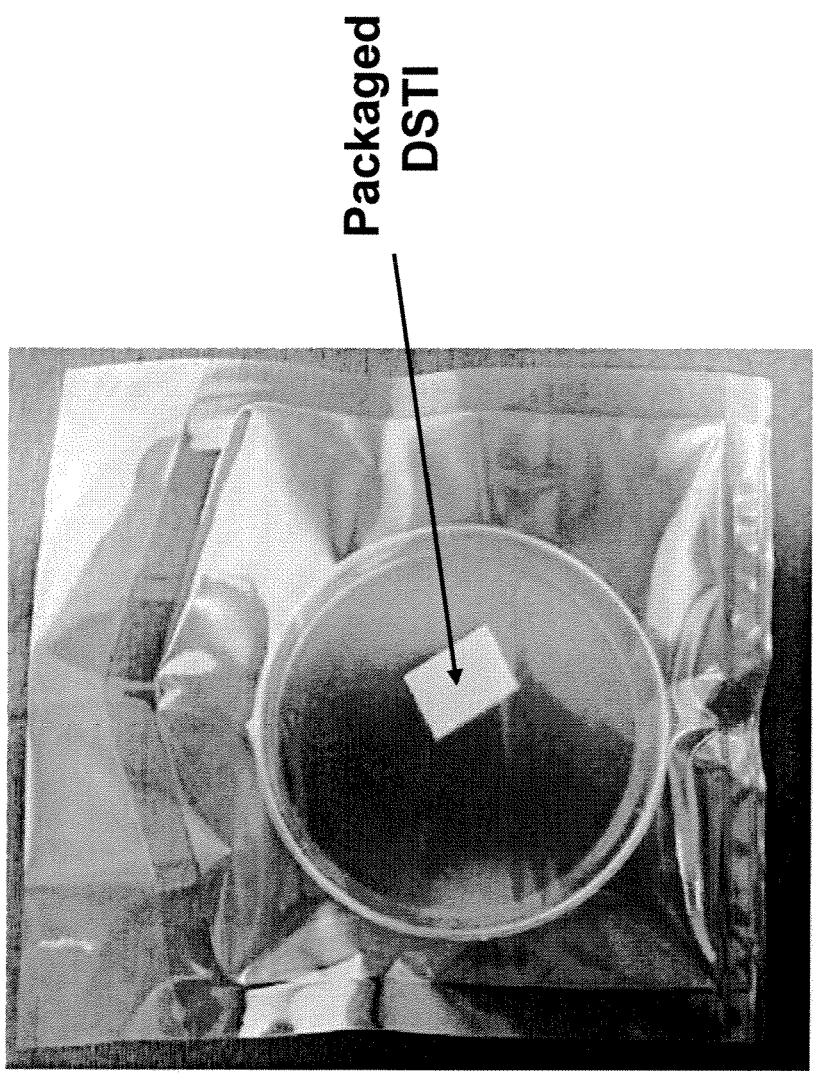
FIG. 1B is a photograph of the double-structured tissue implant (DSTI) packaged in a sterile form ready for delivery wherein said implant may be provided in a dry form optionally comprising covalently bonded drugs or growth factors or in a wet form optionally comprising cells, drugs or growth modulators.

FIG. 1B shows the double-structured tissue implant as a dry sterile product enclosed in a shipping container within sterile packaging. The packaged product is available as an off-the-shelf DSTI for implantation in clinical settings. Alternatively, the DSTI may be prepared in a sterile wet rehydrated form optionally containing cells, drugs or modulators and delivered to a surgeon in a ready-to-use form.

I. Double-Structured Tissue Implant

A double-structured tissue implant (DSTI) comprises two separately prepared components, namely the primary scaffold that provides a structural support for the secondary scaffold incorporated within the primary scaffold.

A. The Primary Scaffold

The primary scaffold is a collagen-based matrix prepared as a honeycomb, lattice, sponge or any other similar structure made of a biocompatible and/or biodegradable collagen containing material of defined density and porosity that is pliable, storageable and, most importantly, highly porous.

Typically, the primary scaffold is prepared from collagen, collagen-containing composition or collagen containing a polymer. Representative compounds suitable for preparation of the primary scaffold are a Type I collagen, Type II collagen, Type III collagen, Type IV, Type VI collagen, gelatin, collagen containing agarose, collagen containing hyaluronan, collagen containing proteoglycan, collagen containing glycosaminoglycan, collagen containing glycoprotein, collagen containing glucosamine, collagen containing galactosamine, collagen containing fibronectin, collagen containing laminin, collagen containing a bioactive peptide growth factor, collagen containing cytokine, collagen containing elastin, collagen containing fibrin, collagen containing polylactic, polyglycolic or polyamino acid, collagen containing polycaprolactone, collagen containing polypeptide, or a copolymer thereof, each alone or in combination with other collagen, such as Type IX and XI.

Additionally, the primary scaffold may be prepared from the collagen precursors, such as, for example, peptide monomers, such as alpha 1 (type I), and alpha 2 (type I) collagen peptide or alpha 1 (type I) alpha 2 (type I) peptides, alone or in combination, or from a combination of precursors, such as 2 (alpha 1, type I) peptide and 1 (alpha 2, type I) peptide.

The collagen containing material used for preparation of the primary scaffold may further be supplemented with other compounds, such as pharmaceutically acceptable excipients, surfactants, buffers, additives and other biocompatible components.

Preferably, the primary scaffold of the invention is prepared from collagen and most preferably from Type I collagen or from a composition containing Type I collagen.

In one embodiment, the primary scaffold is a structure containing a plurality of narrowly defined randomly or non-randomly organized pores having a substantially homogeneous narrowly defined size and diameter that are uniformly distributed through the scaffold, dividing the scaffold space into columns or pore network. Under the most favorable conditions, the pores are through and mostly vertically oriented, and represent a high percentage of the total volume of the scaffold. The exemplary primary scaffold is described in the co-pending application Ser. No. 11/523,833, filed on Sep. 19, 2006, herein incorporated by reference in its entirety.

In another embodiment, the primary scaffold may be the Type I collagen-based support matrix that is a collagen-based porous honeycomb, sponge, lattice, sponge-like structure or honeycomb-like lattice of defined porosity having randomly or non-randomly organized pores of variable pore diameters such as described in, for example, application Ser. No. 10/882,581, filed on Jun. 30, 2004, issued as U.S. Pat. No. 7,217,294 on May 15, 2007, herein incorporated by reference in its entirety.

In yet another embodiment the primary scaffold is a honeycomb collagen matrix developed by Koken Company, Ltd., Tokyo, Japan, under the trade name Honeycomb Sponge, described in the Japanese patent JP3170693, hereby incorporated by reference. The primary scaffold according to the invention has, preferably, a substantially defined pore size in diameter and pore density in randomly or non-randomly organized manner that creates an apical (top) or basal (bottom) surface to the implant where the sizes and diameters of the pores on both the apical or basal surface are substantially the same, that is, at least 70% of the pores have the same size and diameter. When used as a primary scaffold only, the scaffold provides conditions for a sterically-enhanced enablement of cells. Chondrocytes, for example, produce an extracellular matrix comprising glycosaminoglycan and Type II collagen within said implant in ratios characteristic for a normal healthy articular cartilage.

Figure 2:
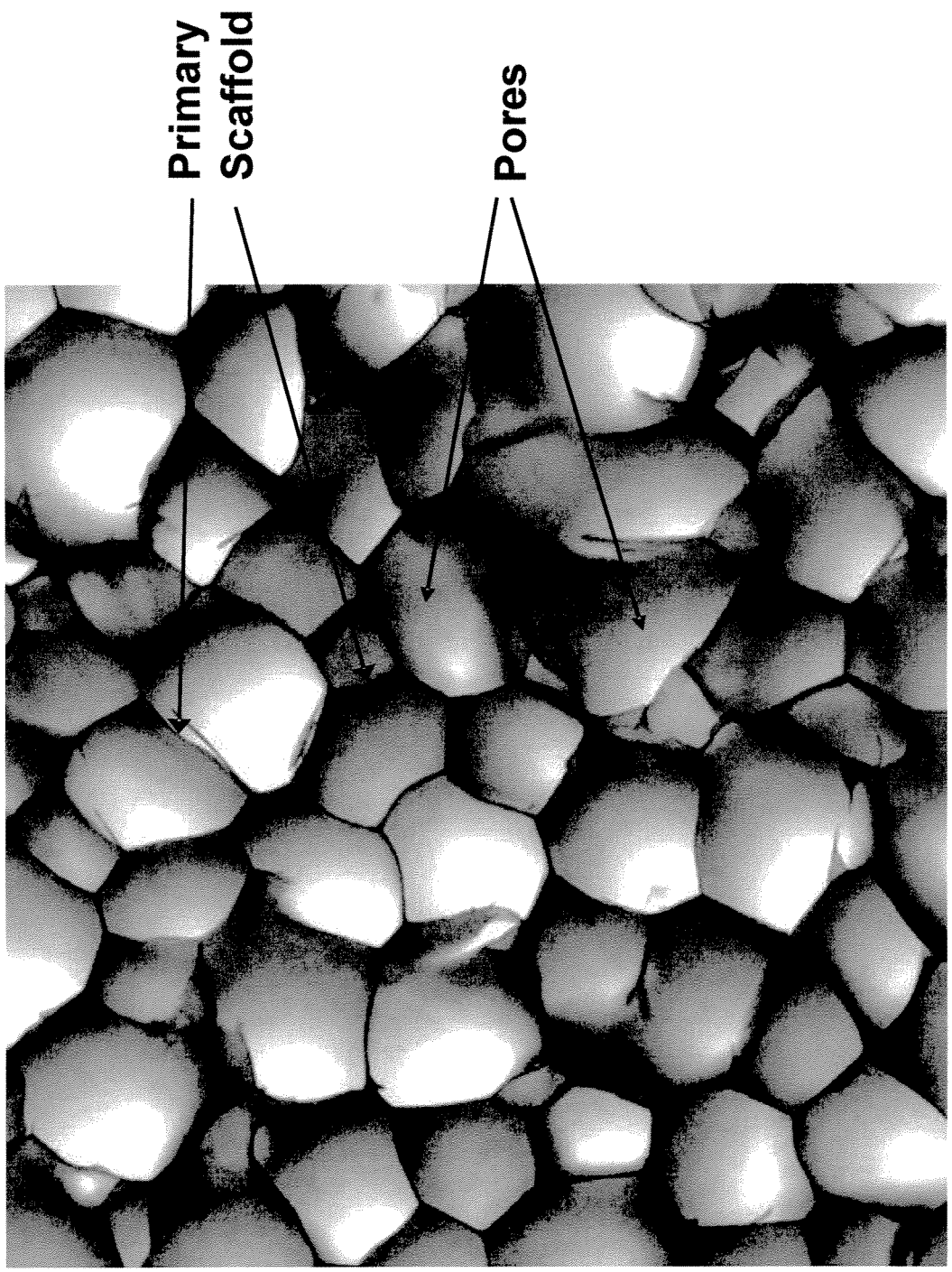
FIG. 2 is a photomicrograph of a primary scaffold showing pores having substantially the same size (4× magnification), said scaffold used as the foundation and structural support for preparation of the double-structured tissue implant. As shown, the primary scaffold has a honeycomb structure of relative uniform pore size and equal distribution.

A microphotograph of the primary scaffold is shown in FIG. 2. FIG. 2 is a representation of one embodiment of the primary scaffold that is obtained and used as the structural foundation for preparation of the double-structured tissue implant. As seen in FIG. 2, the primary scaffold has a porous honeycomb structure of relatively uniform pore size and equal distribution.

A secondary scaffold structure is generated within the pores of the primary scaffold. To that end, the primary scaffold is loaded with a Basic Solution suitable for preparation of the secondary scaffold (Basic Solution). Such Basic Solution comprises a soluble collagen, collagen-containing or collagen-like mixture, typically of Type I collagen, in combination with a non-ionic surfactant. The primary scaffold loaded with the Basic Solution for formation of the secondary scaffold is shown in FIG. 3.

Figure 3:
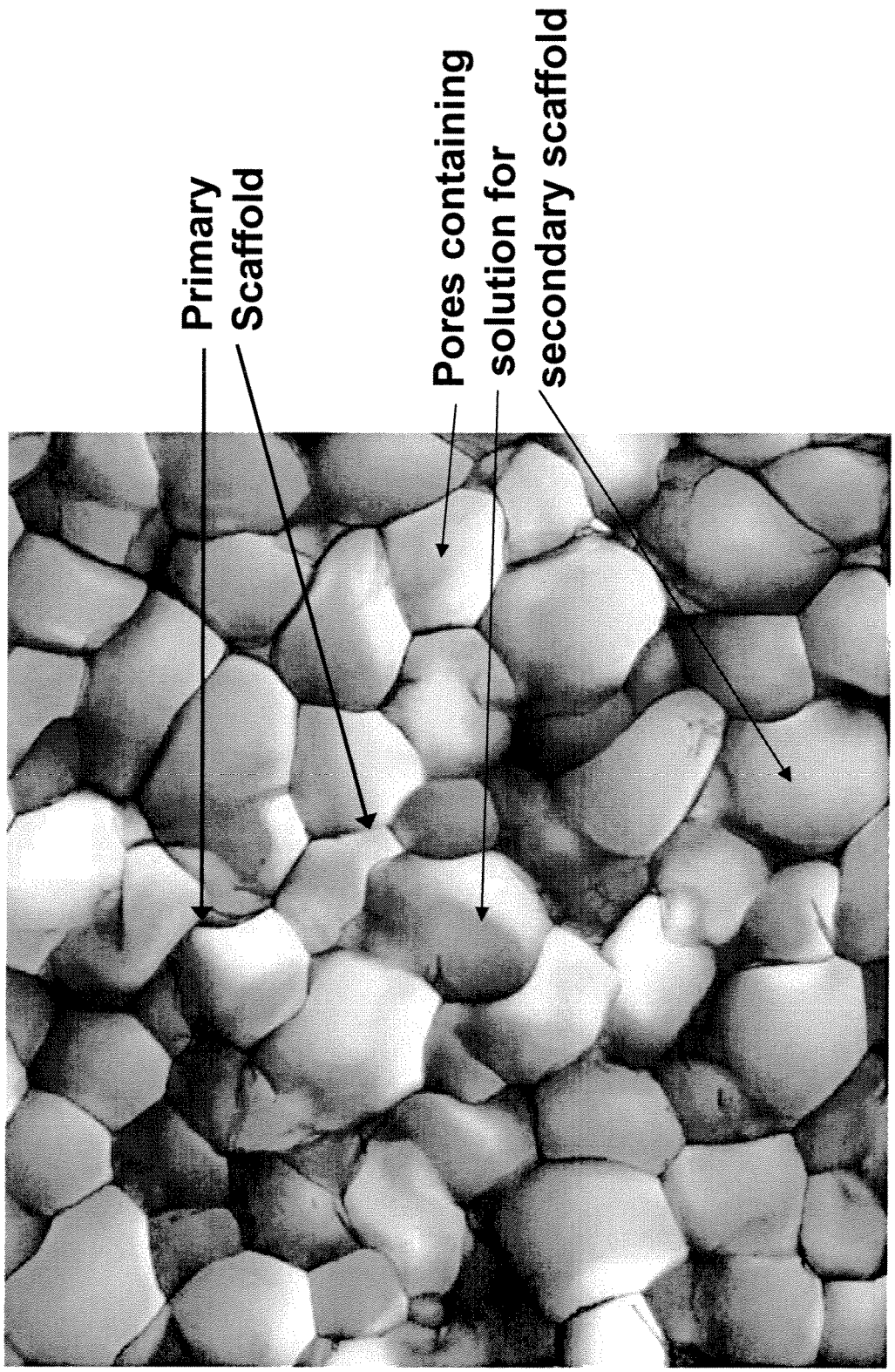
FIG. 3 is a photomicrograph of a primary scaffold having pores loaded with a soluble collagen/PLURONIC® surfactant solution for secondary scaffold (Basic Solution) before precipitation and processing with dehydrothermal treatment (4× magnification) wherein the Basic Solution is prepared and applied as an aqueous gel which evenly fills the pores.

FIG. 3 is a microphotographic representation of the primary scaffold that has been loaded with the Basic Solution comprising solubilized collagen/surfactant composition that forms a basis for formation of the secondary scaffold. The Basic Solution is prepared as a solution, suspension or as an aqueous gel at a dilute acidic pH and is further neutralized to pH 7.4. The Basic Solution is then applied to or is loaded into the primary scaffold such that it evenly fills the porous structure of the primary scaffold.

B. The Secondary Scaffold

The secondary scaffold is created or generated within the pores of the primary scaffold. The secondary scaffold is a qualitatively different structure formed within the confines of the first scaffold or as a stand alone unit (see below).

The secondary scaffold is generated by a process comprising preparing a soluble collagen-based composition as described below, further comprising a suitable non-ionic or ionic surfactant (Basic Solution).

The secondary scaffold comprises a collagen, methylated collagen, gelatin or methylated gelatin, collagen-containing and collagen-like mixtures, said collagen being typically of Type I or Type II, each alone, in admixture, or in combination and further in combination with a surfactant, preferably a non-ionic surfactant. The suitable surfactant is preferably a polymeric compound such as a PLURONIC®-type polymer.

Additionally, the secondary scaffold may be used independently of the primary scaffold as said secondary scaffold stand alone implant or unit where the Basic Solution can be introduced into a mold or container and subjected to precipitation, lyophilization and dehydrothermal treatment.

In preparation of the DSTI, said composition suitable for generation of the secondary scaffold within the primary scaffold is brought into contact with a primary scaffold structure by absorbing, wicking, soaking or by using a pressure, vacuum, pumping or electrophoresis, etc., to introduce said composition for the secondary scaffold into the pores of the primary scaffold. In alternative, the primary scaffold may be immersed into the Basic Solution for the secondary scaffold.

C. Double-Structured Tissue Implant

The double structured tissue implant (DSTI) is prepared by treating the primary scaffold loaded with a Basic Solution comprising combination of the soluble collagen and non-ionic surfactant subjected to a process for preparation of the DSTI described below in Scheme 1.

Briefly, the primary scaffold is loaded with the collagen/surfactant combination, precipitated or gelled, washed, dried, lyophilized and dehydrothermally treated to solidify and stabilize the secondary scaffold within the pores of the primary scaffold.

A dehydrated (dry) and rehydrated double-structured tissue implant is seen in FIGS. 4A and 4B. In these figures, the primary scaffold pores are seen as delineating black lines and the pores of the primary scaffold are filled with the secondary scaffold, where the secondary scaffold is observed from the fibrous-like diffraction pattern present within the pores of the primary scaffold. Such diffraction pattern occurs due to the polymerization of the collagen within the pores. The collagen fibers interdigitate within the pores and among the pores.

The double-structured tissue implant can be seeded with cells, loaded with pharmaceutical agents, drugs or growth modulators. Additionally and preferably, the two of its distinct components, namely the primary scaffold and the secondary scaffold, can each be independently loaded with living cells, cell suspension, with a pharmaceutically effective agent or agents or with growth modulators. These may be loaded into the implant individually or in any possible combination, such as, for example, where the cells may be introduced into one component, for example, into the primary scaffold of the DSTI, and the drug is introduced into the second component, for example, into the secondary scaffold of the DSTI, or the drug is introduced into one component and the modulator into the second component and/or any variation thereof. Both components of the DSTI may be loaded with the same or different agent or with a combination of agents.

Figure 5:
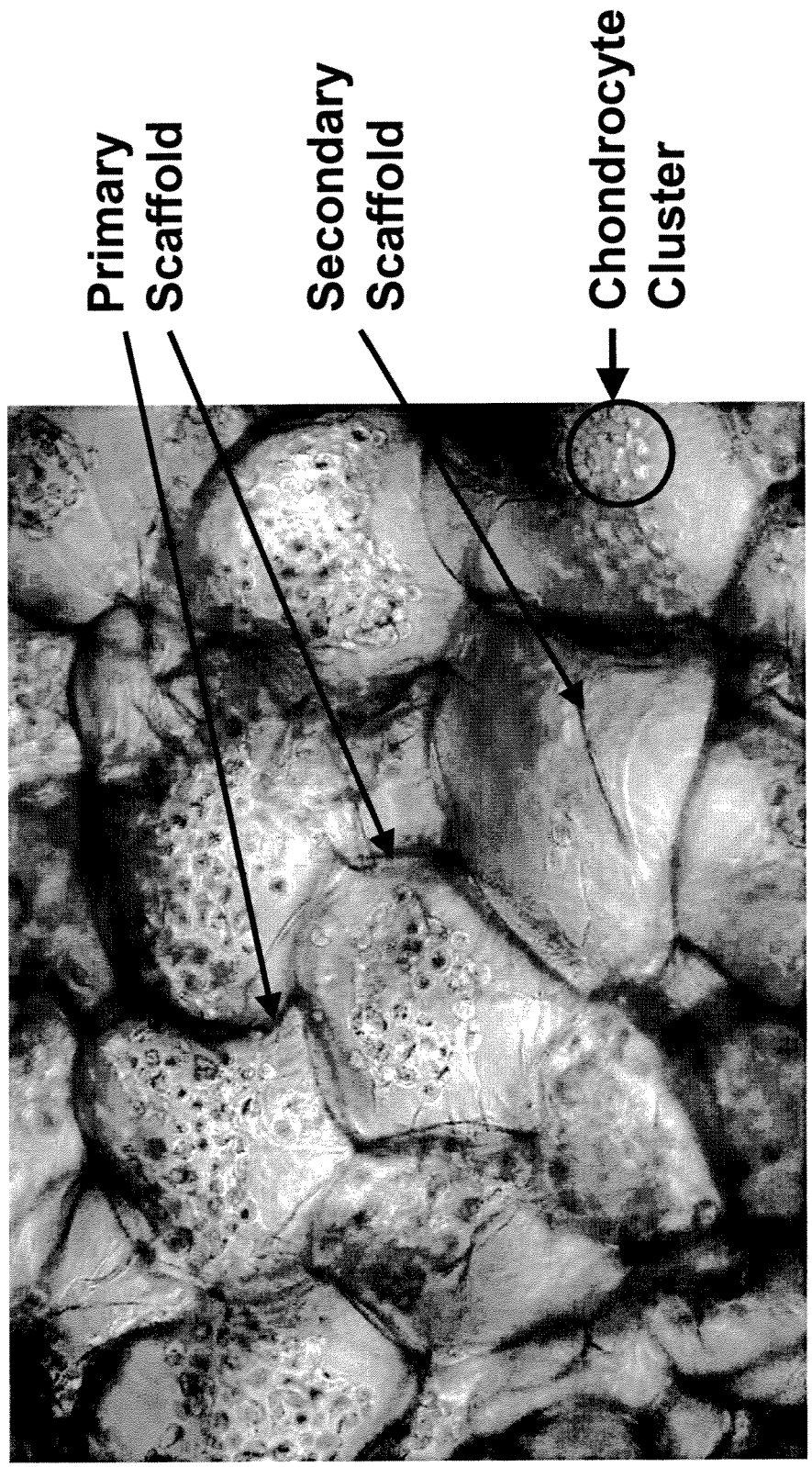
FIG. 5 is a photomicrograph of a double-structured tissue implant seeded with chondrocytes after 14 days in culture showing a primary scaffold, a secondary scaffold and chondrocytes attached to or embedded within the secondary scaffold localized in the pores of the primary scaffold (10× magnification). The DSTI shown in FIG. 5 was dehydrothermally treated and subsequently has undergone rehydration with a phosphate buffered saline and seeding with chondrocytes that were maintained in culture over a period of 14 days. The cultured chondrocytes are shown to adhere to the fibrous secondary scaffold, as well as aggregate within the pores, seen in the upper left corner.

The DSTI loaded with chondrocytes is shown in FIG. 5 wherein the cells are attached to the secondary scaffold.

FIG. 5 is a microphotograph of the dehydrothermally treated double-structured tissue implant that was subjected to rehydration with a solution containing chondrocytes where the chondrocytes were deposited within the DSTI after being maintained in culture over a period of several days. FIG. 5 shows cells adherent to the fibrous secondary scaffold, as well as being present as aggregates within the pores.

D. The Drug Containing Double-Structured Tissue Implant

The double-structured implant of the invention provides for a variability of uses. One embodiment of the use is the double-structured tissue implant containing the pharmaceutical agent, drug, growth modulator, growth hormone, mediator, enzyme promoting cell incorporation, cell proliferation or cell division, pharmaceutically acceptable excipient, additive, buffer etc.

The drug may be introduced separately into the primary scaffold, into the secondary scaffold, or both, or be added at a time of rehydration to a composition for the secondary scaffold before its processing. Because of the collagen structure of the DSTI, drugs or modulators may be bonded to the DSTI through a covalent linkage, such as for example, amide or ester bonds, or ionic charge or hydrogen bonding.

The pharmaceutical agents, drugs or modulators are selected from the group consisting of:

growth and morphogenic factors, such as, for example, transforming growth factor, insulin-like growth factor 1, platelet-derived growth factor, bone morphogenetic proteins (bmps);

cytokines, such as, for example, interleukins, chemokines, macrophage chemoattractant factors, cytokine-induced neutrophil chemoattractants (gro-1), integral membrane proteins such as integrins and growth factor receptors;

membrane associated factors that promote growth and morphogenesis, such as, for example, repulsive guidance molecules;

cell attachment or adhesion proteins, such as, for example, fibronectin and chondronectin;

hormones, such as, for example, growth hormone, insulin and thyroxine;

pericellular matrix molecules, such as perlecan, syndecan, small leucine-rich proteoglycan and fibromodulin;

nutrients, such as, for example, glucose and glucosamine;

nucleic acids, such as, for example, RNA and DNA;

anti-neoplastic agents, such as, for example, methotrexate and aminopterin;

vitamins, such as, for example, ascorbate and retinoic acid;

anti-inflammatory agents, such as, for example, naproxen sodium, salicylic acid, diclofenac and ibuprofen;

enzymes, such as, for example, phosphorylase, sulfatase and kinase; and metabolic inhibitors, such as, for example, RNAi, cycloheximide and steroids.

These, and other similar compounds and/or compounds belonging to the above-identified groups may be added individually or in combination to a primary scaffold, to a secondary scaffold, to a composition (Basic Solution) for formation of the secondary scaffold or to the lyophilized composite or DSTI before, during or after implantation.

Addition of agents such as growth factors, cytokines and chemokines will increase cell migration, cell growth, will maintain or promote appropriate cell phenotype and will stimulate extracellular matrix synthesis. Loading the scaffold with anti-inflammatory agents or other drugs can provide a local site-specific delivery system.

The range of concentration of the added drug or compound depends on the drug or compound and its function and it extends from picograms to milligrams.

E. Cellular Deposition

The DSTI has the capacity for preloading of differentiated or undifferentiated cells to augment tissue repair. In the case of differentiated cells, chondrocytes, osteoblasts, tenocytes, fibroblasts, fibrochondrocytes and ligament cells can be isolated and applied by infusion, dropwise, wicking, pumping or injection, for healing of cartilage, bone, tendon, skin, meniscus or ligament, respectively, or for other tissue defects.

In the case of undifferentiated cells, adult or immature mesenchymal cells derived from bone marrow aspirates, iliac crest needle biopsies or other dissociable mesenchymal tissues, such as somites, muscle, interstitial connective tissues, through enzymatic dissociation and subsequent culture, can be applied in methods similar or identical to differentiated cells. Other mature or immature undifferentiated cells may be from immortalized cell lines, hematopoietic stem cells, neural stem cells each having the capacity for differentiation in situ or may include embryonic stem cells which when isolated and placed within the localized defect can undergo differentiation to the target tissue.

The number of cells to be applied may vary in accordance with the differentiated state of the cells and with their inherent proliferative capacity. The age of the cells may vary with origin and with time in culture.

F. Secondary Scaffold as a Stand Alone Implant

In one embodiment, the secondary scaffold may be generated as a stand alone structure. In this regard, a composition comprising a soluble collagen, methylated collagen, gelatin or methylated gelatin in an acidic solution further comprising a non-ionic surfactant is subjected to neutralization, precipitation, dehydration, lyophilization and dehydrothermal treatment under conditions as described in the Scheme 1.

As described for the double structured tissue implant, the secondary scaffold as a stand alone implant may be similarly loaded with cells and may optionally contain a pharmaceutical agent, growth modulator or another compound before or after implantation, as described above.

The process for preparation of the stand alone secondary scaffold is modified to the extent that the composition for preparation of the secondary scaffold (Basic Solution) is placed into a container suitable to permit gelling, precipitation, dehydration, lyophilization and dehydrothermal treatment.

The stand alone secondary scaffold is used for implantation in the same manner as described for double-structured tissue implant. The stand alone secondary scaffold is useful in the healing of tears in cartilage or skeletal tissues, such as, for example, the meniscus where it can be charged and/or supplemented with all of the tissue factors and cells, such as meniscal fibroblasts.

The stand alone secondary scaffold can be used in a similar fashion for bone, tendon and ligament repair.

Components and conditions suitable for preparation of the secondary scaffold stand alone structure and evaluation of its performance using cell viability are seen in Table 1.

TABLE 1

| Collagen conc. (mg/ml) | Plutonic F127 conc. (mg/ml) | DHT, 6 h at 140° C. | Rehydration time (s) | Dissolution stability in PBS at 37° C. | Cell viability (%) |
|---|---|---|---|---|---|
| Precipitated or gelled using ammonia vapor | | | | | |
| 3 | 0.25 | Y | 12 | Stable | — |
| 3 | 1 | Y | 13 | Stable | — |
| 3 | 1 | Y | <10 | Stable | 97 |
| 3 | 1 | N | <10 | Dissolved | — |
| 3 | 3 | Y | <10 | Stable | 98 |
| 3 | 3 | N | <10 | Dissolved | — |
| 2.9 | 0.29 | Y | 6 | Stable | — |
| 2.9 | 0.29 | N | 3 | Dissolved | — |
| 2 | 0.165 | Y | 7 | Stable | — |
| 2 | 0.33 | Y | 3 | Stable | — |
| 2 | 0.67 | Y | 2 | Stable | — |
| 2 | 0.25 | Y | 15 | Stable | — |
| 2 | 0.5 | Y | 7 | Stable | — |
| 2 | 0.1 | Y | 4 | Stable | — |
| 2 | 2 | Y | <10 | Stable | 99 |
| 2 | 2 | N | <10 | Dissolved | — |
| 1.5 | 0.15 | Y | <10 | Dissolved | — |
| 1.5 | 0.15 | N | 16 | Dissolved | — |
| Precipitated or gelled using NaOH | | | | | |
| 2.3 | 0.05 | Y | 23 | Stable | — |
| 2.3 | 0.1 | Y | 19 | Stable | — |
| 2.3 | 0.23 | Y | 15 | Stable | — |
| 2.4 | 0.24 | Y | 5 | Stable | — |

Table 1 summarizes experimental conditions used for determination of optimization of conditions for preparation of a secondary scaffold. The conditions tested and evaluated were a collagen concentration, surfactant concentration, temperature and time for dehydrothermal treatment (DHT), rehydration time, stability of the DSTI determined by dissolution of the secondary scaffold in phosphate buffer saline at 37° C., and cell viability.

The secondary scaffold was precipitated in the presence of ammonia vapor or ammonia aqueous solution or in the presence of 0.1M sodium hydroxide (NaOH)

Results seen in Table 1 show the effectiveness of dehydrothermal treatment for preparation of secondary scaffolds, in terms of achieving the stability of the secondary scaffold, its fast rehydration and assuring cell viability within the secondary scaffold.

As seen from the results summarized in Table 1, following ammonia precipitation of the collagen, dissolution stability was not observed in the absence of dehydrothermal treatment in spite of varying collagen and surfactant concentrations. In instances where stability was achieved, there was excellent cell loading and viability at collagen concentrations greater than 1-5 mg/ml and at surfactant concentrations of 1, 2 and 3 mg/ml.

In an alternative approach, the precipitation of collagen by neutralization with NaOH, in the presence of Pluronic surfactant and subject to DHT, detected formation of a rapidly rehydrating and stable secondary scaffold.

These results clearly show that the properties of the secondary scaffold alone or the secondary scaffold incorporated into the DSTI may be conveniently optimized to achieve fast rehydration time, dissolution stability and excellent cell loading and cell viability up to 99% within the secondary scaffold.

G. Surfactants

Improved properties of the DSTI, such as its rapid wettability and resistance to shrinkage, swelling and dissolution, are due to a presence of a secondary scaffold as a distinct functional entity.

The secondary scaffold prepared according to the process of the invention requires, as an essential part, a presence of a surfactant, preferably a non-ionic or, in some instances, even an ionic surfactant. The surfactant, preferably the non-ionic surfactant of type such as TRITON® or PLURONIC®, preferably PLURONIC® F127, is an essential component of a composition used for preparation of the secondary scaffold, or micellar substrate bound to the implant. The presence of the surfactant improves stability and particularly wettability and rehydration properties of the implant without causing its shrinkage or swelling.

Suitable surfactants, such as PLURONIC®-type polymers or TRITON®-type polymers, are non-ionic co-polymer surfactants consisting of polyethylene and polypropylene oxide blocks.

TRITON®-type surfactants are commercially available derivatized polyethylene oxides, such as for example, polyethylene oxide p-(1,1,3,3-tetramethylbutyl)-phenyl ether, known under its trade name as TRITON®-X100. Other TRITON®-type surfactants that may be suitable for use in the instant invention are TRITON® X-15, TRITON® X-35, TRITON® X-45, TRITON® X-114 and TRITON® X-102. TRITON® surfactants are commercially available from, for example, Union Carbide, Inc.

PLURONIC®-type surfactants are commercially available block co-polymers of polyoxyethylene (PEO) and polyoxypropylene (PPO) having the following generic organization of polymeric blocks: PEO-PPO-PEO (Pluronic) or PPO-PEO-PPO (Pluronic R). Exemplary PLURONIC®-type surfactants are PLURONIC® F68, PLURONIC® F127, PLURONIC® F108, PLURONIC® F98, PLURONIC® F88, PLURONIC® F87, PLURONIC® F77, PLURONIC® F68, PLURONIC® 17R8 and PLURONIC® 10R8. The most preferred non-ionic surfactant of PLURONIC®-type suitable for use in the invention is a block co-polymer of polyoxyethylene (PEO) and polyoxypropylene (PPO) with two 96-unit hydrophilic PEO blocks surrounding one 69-unit hydrophobic PPO block, known under its trade name as PLURONIC® F127. PLURONIC® surfactants are commercially available from BASF Corp.

H. Properties of the Double-Structured Tissue Implant

The DSTI of the invention has distinctly improved properties when compared to the primary scaffold alone, to the secondary scaffold alone or to a composite loaded with a composition for preparation of the secondary scaffold (Composite), unprocessed, or to the Composite that has been dehydrated and lyophilized (Lyophilized Composite).

Typically, a tissue implant is implanted into a tissue defect during a surgery either already rehydrated (wet) or in a dry form. Also typically, such surgery has a time-limit on implantation that has about one hour window when the implant needs to be placed into the defect. For these reasons, it is important that a specification for an implantable double-structured tissue implant provides stability, resistance to change in shape, size and shrinkage or swelling, resistance to dissolution, consistency with respect to pore size permitting an ingrowth of cells into the implant and conditions for formation of extracellular matrix within the implant. The DSTI appears to have all the above properties.

Furthermore, a presence of the secondary scaffold improves the function of the DSTI by providing a multitude of small membranous substrates which can provide cell anchorage and phenotype stability while preserving the through porosity of the overall implant, thereby allowing nutrients and growth factors and migratory cells to permeate the implant.

In the case of cartilage lesion the migratory cells include chondrocytes from the debrided lesion which have been freed from damaged extra-cellular matrix through the upregulation of certain matrix metalloproteinases.

I. Stability of the Double-Structured Tissue Implant

From the point of view of the implantability, stability of the implant is one of the major requirements. The implant stability depends on several factors. There must be minimally low or, preferably, almost no initial dissolution of collagen from the implant into the physiological fluids and there must be minimally low or preferably no change in size and shape of the implant following rehydration or wetting before, during or after surgery prior to biodegradation in situ.

DSTI of the invention has a very minimal initial collagen dissolution and a minimal change in size and shape during the initial critical period.

2. Collagen Retention and Resistance to Dissolution

One of the most important requirements for the implant is its resistance to dissolution of its components upon wetting and rehydration of said implant during implantation during preparation of the implant for implantation and subsequently also after implantation. A minimally low dissolution or, preferably, almost no dissolution of the collagen component from the implant into the physiologic solution after or before placement of the implant into the tissue defect, and into an interstitial fluid, plasma or blood following the surgery, under normal physiological conditions ensures continued functionality of the implant following its implantation into the tissue defect, such as, for example into the cartilage lesion. Low or no dissolution of collagen from the implant means the high retention of the collagen within the implant.

Figure 6:
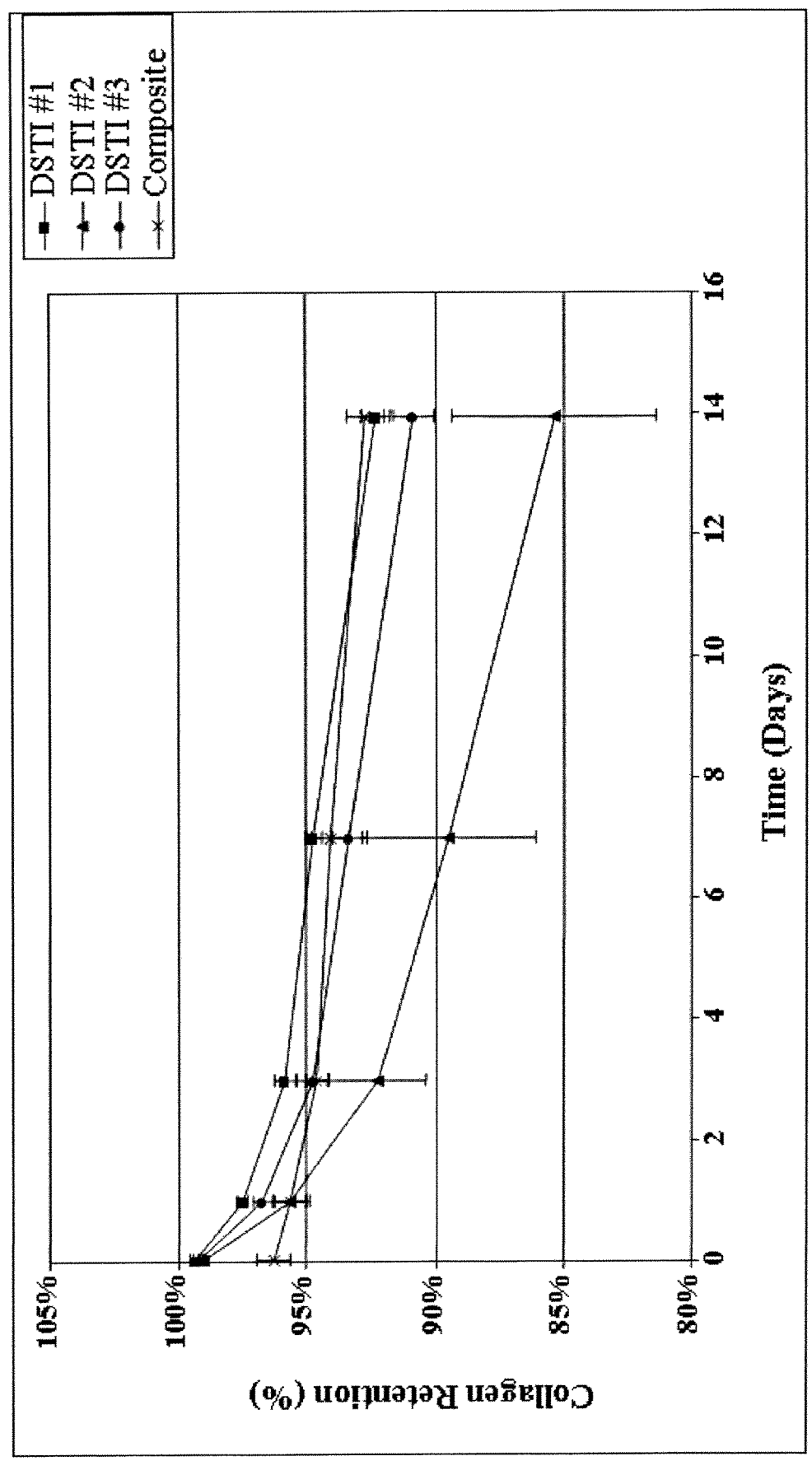
FIG. 6 is a graph demonstrating collagen retention in phosphate buffered saline, and its resistance to dissolution from three separate double-structured tissue implants (DSTIs) compared to a composite consisting of a primary scaffold loaded with a composition for a secondary scaffold but not lyophilized or dehydrothermally processed (Composite).

FIG. 6 demonstrates the structural stability of the collagen network present in the double-structured tissue implant as a function of time following rehydration of the implant with an aqueous phosphate buffered saline solution by comparing collagen retention, in percent, within DSTI, to collagen retention within an unprocessed composite (Composite) comprising a primary scaffold loaded with a composition for a secondary scaffold (Basic Solution) but not lyophilized or dehydrothermally processed.

Results seen in FIG. 6 demonstrate the structural stability of the collagen network present in the double-structured tissue implant as a function of time in an aqueous buffered saline solution. The data demonstrate that during the first day following the rehydration, there is very little dissolution of collagen from the DSTIs (D #1-3) and that the retention of collagen is almost 100% during the same initial first critical hour. On the other hand, the dissolution from the Composite (-x-) in the initial hour is much higher and the collagen retention drops immediately to approximately 96% during that same critical first hour although it stabilizes later on. FIG. 6 thus clearly demonstrates stability of the DSTI.

In order to determine the stability of the implant subjected to transport and handling, another study was performed with and without agitation and the dissolution of collagen from of DSTI under these conditions was compared to the dissolution of collagen from the non-lyophilized composite (Composite). Results are not shown. These studies confirmed that even with agitation, there is a relatively small change in the accumulated release of protein into the solution over a period of eight days but particularly during the first hour following the rehydration.

3. Resistance to Change in Size and Shape

Another important feature of the DSTI is its resistance to change in size and shape. This feature is very important for implant efficacy as any change in the size and shape by shrinking or swelling can negatively affect the outcome of the implantation surgery. An implant that would get smaller by shrinking will not fill the defect, will not provide a structural support for migration of cells from the surrounding tissue or cell integration into the surrounding tissue and may also be dislodged from the defect. Swelling of the implant could, on the other hand, cause the implant to swell within the defect, decrease the structural support for cells and be rejected or ejected from the defect because of its larger size.

The resistance to change in shape and size means that for implantation into a defect of discernable size, the functional construct must not swell or shrink extensively upon rehydration during time of preparation before surgery or after placement of the implant into the defect.

Figure 7:
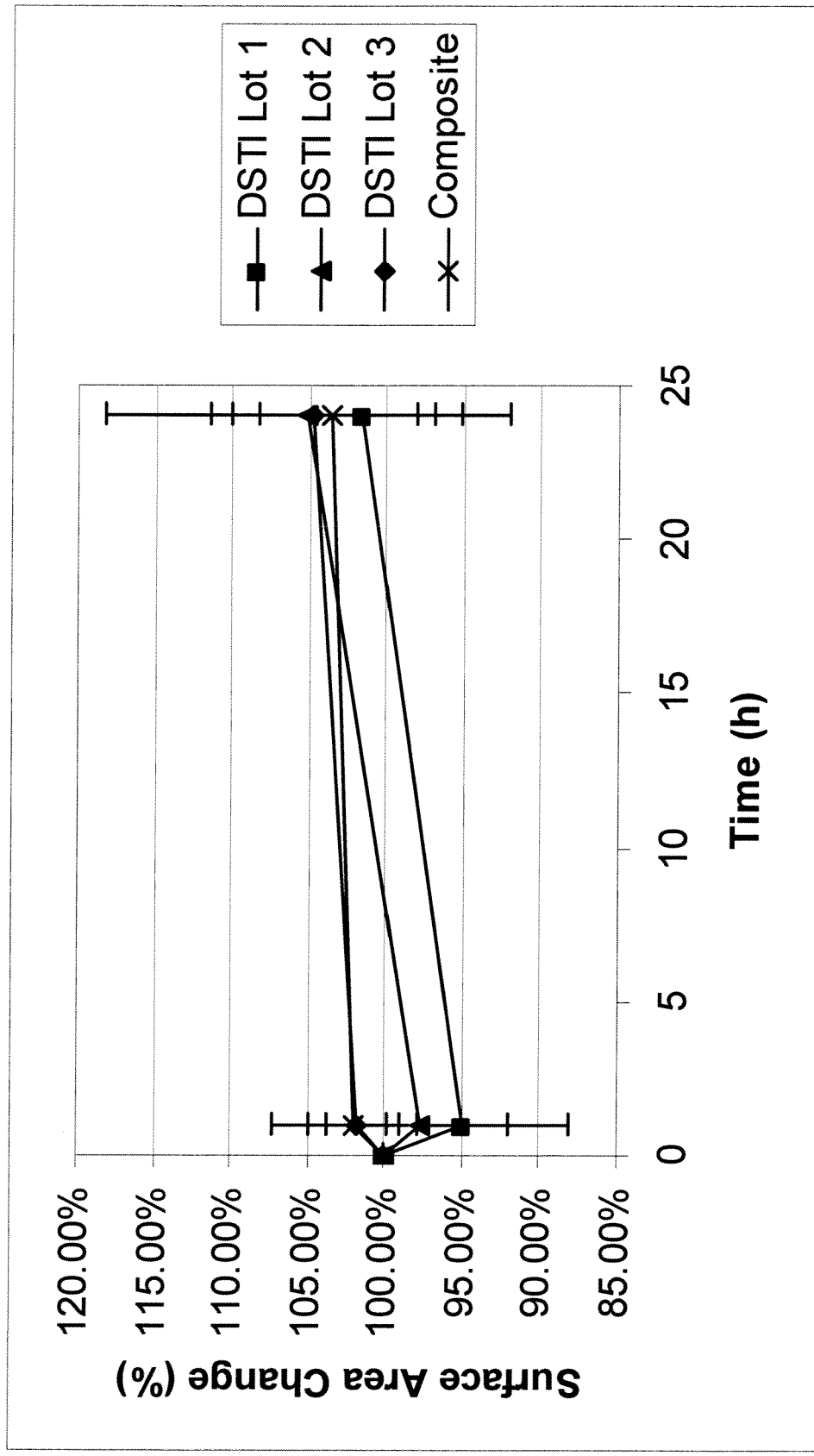
FIG. 7 is a graph illustrating percent of surface area change of double-structured tissue implant (DSTI) and a composite (Composite) of a primary scaffold loaded with a composition for a secondary scaffold before lyophilization and dehydrothermal processing, from 1 to 24 hours. The implants were rehydrated with an aqueous phosphate buffered saline and maintained in culture for eight days. Results show that there is an insignificant small change in the surface area during the first hour following the rehydration in both DSTI and Composite. This figure confirms that in the double-structured tissue implants (DSTI) subjected to the dehydrothermal treatment there is a very small change in the surface area and therefore no shrinkage or swelling following the rehydration.

FIG. 7 presents the percent change in surface area of DSTI, rehydrated with and maintained in culture for more than 24 hours in an aqueous phosphate buffered saline. The results seen in FIG. 7 show that there is very little change in size and shape during the critical first hour in DSTI. In three lots of double-structured tissue implants subjected to the dehydrothermal treatment there was approximately a 2-5% change in surface area within the first hour and such change was maintained within these parameters for more than 24 hours following the rehydration.

4. Cell Viability

Another important feature of the tissue implant is to provide support and conditions for cell migration from surrounding tissue or for the cell integration into surrounding tissue in the case when the cells are seeded into the DSTI before implanting. This feature is determined by cell viability within the DSTI and provides another criteria for determining functionality and usefulness of the DSTI.

In order for an implant to be functionally viable, the implant must provide a structural support for cells as well as provide or permit conditions to be provided for cell seeding into the implant, cell growth within the implant and/or cell migration into or from the surrounding tissue. Conditions for cell seeding, their growth within the implant, their nutritional and metabolic needs are designed based on the type of cells that the implant is supposed to deliver and support. For example, if the implant is designed for repair of a skin defect, the cells and their requirement will be different than if the implant is designed for repair of a chondral or bone lesion. Conditions for structural support and conditions for promotion of cell growth, their migration and/or integration into the surrounding tissue will be adjusted based on the tissue where the DSTI will be implanted and the function the implant will assume in repair of the tissue defect.

While the DSTI of the invention is preferably suitable for use in treatment and repair of chondral, subchondral or bone lesions, the DSTI, as such, is suitable to be used for repair of any other tissue or tissue defect.

To determine the cell survival within the DSTI, studies were performed to determine the cell viability by determining their survival and growth within the DSTI. Cell viability was determined for three lots of DSTI that had been seeded with chondrocytes after 1 day and 21 days in culture. Results are seen in FIG. 8.

FIG. 8 shows production of sulfated glycosaminoglycan and DNA (S-GAG/DNA) by chondrocytes seeded in double-structured tissue implant (DSTI) and in a composite (Composite) comprising a primary scaffold loaded with a composition for a secondary scaffold before lyophilization and dehydrothermal processing, after 14 days in culture.

Results seen in FIG. 8 demonstrate that inclusion of the secondary scaffold within DSTI supports the growth of cells and deposition of extracellular matrix measured here as production of sulfated glycosaminoglycan. A comparison between the double-structured tissue implant and the Composite showed comparable results with little evidence of significant steric hindrance due to the added structural components. All samples had 96-100% viability at both timepoints indicating no cell toxicity. Furthermore, as with the DNA measurements, the total cell number increased over time which shows that the cells were retained in the DSTI, were viable and proliferated to fill the pores.

5. Pore Size

The successful implant, such as, for example, wet or dry DSTI implanted into the cartilage lesion, must provide conditions allowing cells to form and generate a new extracellular matrix. In this regard, the implant porous structure must allow cells to migrate, be attached or aggregate into and within the pores and to function similarly to their normal function in the healthy tissue.

Consequently, the pore size of the implant and the consistency with respect to pore size for the ingrowth of cells is important both for cell adhesion, extracellular matrix production and cell to cell contact and communication. Depending on the tissue to be repaired, the pore size of the primary and/or secondary scaffold will vary. For example, cartilage scaffolds would have an optimal pore size of approximately 200 μm and bone would have a pore size in the range of 300 to 350 μm.

A significant advantage of having a double-structured tissue scaffold arises from the increase in mechanical integrity relative to a primary porous collagenous material because the polymerization creates fiber-like structure between the primary and secondary scaffold that serves as a reinforcing network for cells.

6. Surface Area

In addition, due to inclusion of the secondary scaffold there is an increase in overall surface area within the DSTI that permits cells spreading and migration throughout the interstices of the DSTI. At the same time, the secondary scaffold must be designed such that it is not of such high density that it becomes a blocking agent that acts as a steric hindrance for cell ingrowth and tissue repair.

The double-structured tissue implant of the invention provides optimal conditions, such as implant stability, collagen retention, resistance to change in size and shape of the implant, pore size and surface area for viability and growth of cells within the implant.

II. Process for Preparation and Use of the Double-Structured Tissue Implant

The secondary scaffold is generated within confines of the primary scaffold by a process comprising several stages and steps as set forth in Scheme 1. The process stages comprise pre-loading, loading, polymerization, treatment of composite double-structured scaffold, dehydrothermal treatment, packaging and surgical procedure.

Scheme 1

Process for Production and Use of a Double-Structured Implant

Stage 1—Pre-Loading

The pre-loading stage is a preparatory stage where the primary scaffold is either obtained from commercial sources or is prepared according to the procedure described in Example 1

Step 1

Step 1 comprises obtaining or preparing a primary scaffold, typically a collagen containing honeycomb, sponge or lattice providing a structural support for incorporation of the secondary scaffold.

In one embodiment, a bovine Type I collagen matrix with honeycomb (HC) like structure is obtained, for example, from Koken, Inc. (Japan) or from other commercial sources and used as primary scaffold. However, such commercially available honeycomb matrices have typically randomly distributed pores of irregular shape and size. The pores of these structures are not always vertically positioned.

In another embodiment, and preferably, a primary honeycomb scaffold is produced according to a process described in Example 1, wherein said primary scaffold has randomly or non-randomly oriented pores of substantially the same size and shape.

The shape and size of the primary scaffold determines a size of the double-structured tissue implant (DSTI) ultimately delivered to the surgeon for implantation into the tissue defect.

Typically the DSTI has a rectangular, circular or oval shape with dimensions of about 50 mm and a vertical thickness of about 1 to 5 mm, preferable 1-2 mm. Preferred dimensions of the DSTI for its preparation and, therefore, the dimensions of the primary scaffold are 50×50 mm×1.5 mm, with pores oriented substantially vertically, said pores having a pore size of from about 100 to about 400 μm, preferably about 200±100 μm and pore length of 1.5 mm. However, dimensions of the primary scaffold may be any that are required by the tissue defect to be repaired and that can be prepared by the process of the invention.

Step 2

Step 2 comprises preparing a composition for preparation of a secondary scaffold (Basic Solution) and comprises neutralization of a soluble collagen solution having an initial acidic pH of about pH 1.5-4, preferably between about pH 1.9-2.2, a collagen concentration from about 0.5 to about 10 mg/ml of collagen, preferably about 2.9 to about 3.2 mg/ml, a surfactant concentration from about 0.05 to about 10 mg/ml, preferably about 0.29 to about 0.32 mg/ml and osmolality from about 20 to about 400 mOsm/kg, preferably about 28 to about 32 mOsm/kg. The soluble collagen solution is then neutralized with any suitable base and/or buffer to pH in a range from about pH 7.3 to about pH 7.7 to derive the Basic Solution. Preferably, the solution is neutralized by adjusting pH to neutrality 7.4 using a collagen/surfactant, 10× Dulbecco's phosphate buffered saline (DPBS) and 0.1 M NaOH in 8:1:1 ratio or using an aqueous solution or ammonia vapor in concentration sufficient to neutralize acid within the collagen solution. The final osmolality and pH of the Basic Solution is about 290 mOsm/kg and pH 7.4, respectively.

The suitable buffers for solubilization of the Type I collagen are, for example, a formic acid containing buffer at pH 4.8, acetic acid containing buffer at pH 5.0 or a diluted hydrochloric acid containing buffer at pH 3.0.

Neutralization is typically carried out using ammonia aqueous solution or a vapor of ammonia, or in concentration sufficient to neutralize the acidic pH over about 30 minutes to about 24 hours, preferably for 12 to 24 hours. This factor has also been found to affect the collagen polymerization and formation of pores having homogeneous pore size. However, other means of neutralization may also be conveniently used.

Stage 2—Loading and Precipitation

The primary scaffold is loaded with a Basic Solution for the secondary scaffold comprising soluble collagen solution containing a surfactant. This Basic Solution is subsequently precipitated within pores of the primary scaffold.

Loading the primary scaffold with the Basic Solution for the secondary scaffold is performed using any suitable method. Soaking, wicking, submerging the primary scaffold in the solution, electrophoresis and any other suitable means. Once the Basic Solution for the secondary scaffold is introduced into the primary scaffold, a composite of both is subjected to a process or treatment that results in formation of the secondary scaffold inside pores of the primary scaffold.

Step 3

The neutralized Basic Solution of step 2 is loaded into the primary scaffold by placing from about 3.75 to about 7.5 ml (approximately 1 to 2× volume), preferably a volume about 4.9 ml (approx. 1.3× volume of the primary scaffold) of the secondary scaffold Basic Solution on the bottom of a dish and then placing the primary scaffold in this solution and allowing it to be soaked up.

Stage 3—Polymerization of a Soluble Collagen within a Primary Scaffold

The primary scaffold loaded with the neutralized Basic Solution comprising the soluble collagen and the surfactant is then subjected to conditions resulting in precipitation of the neutralized Basic Solution within the pores of the primary scaffold thereby generating a structurally distinct secondary scaffold (Composite).

Typically, and allowing for variability of the Basic Solution or composition used for creating of the secondary scaffold, the composition introduced into the pores of the primary scaffold is gelled or precipitated within said primary scaffold and may also be cross-linked using chemicals such as glutaraldehyde or another multifunctional aldehyde, where the aldehyde reacts with amino groups of the collagen yielding a Schiff base, which can be stabilized by a reduction reaction; carbodiimide reagent, such as carbodiimide 1-ethyl-3-(3-dimethyl aminopropyl)-carbodiimide (EDC) with or without N-hydroxy-succinimide (NHS) where the HNS is used to suppress side reactions. Additionally, EDC and NHS can be used in combination with diamine or diacid compounds to introduce extended cross-links; acyl azide where the acid are activated and subsequently reacted with an adjacned amine group; epoxy compounds such as 1.4-butanediol diglycidyl ether, or cyanamide.

In addition, irradiation such as short wave length UV irradiation (254 nm) can introduce cross-links in the collagen. The primary scaffold loaded with the Basic Solution (neutralized collagen/surfactant solution) in a range from about 1 to about 2 volumes of the primary scaffold is then placed in an incubator at a temperature from about 25° C. to about 38° C., preferably to about 37° C. temperature, typically for from about 10 minutes to about 18 hours, more typically for about 20 to about 100 minutes, preferably for about 40 to 60 minutes, and most preferably for a time when the precipitation of the neutralized collagen solution into a solid secondary scaffold occurs.

Step 5

In order to assure that the vast majority of the salt of the precipitated collagen solution within the pores of the primary scaffold is removed, a composite consisting of the primary scaffold having the secondary scaffold precipitated within is subjected to a washing step whereby the majority of the salts are removed.

The composite (Composite) comprising the primary scaffold and the secondary scaffold precipitated within, is washed by placing said composite in a volume of from about 20 ml to about 10 liters, preferably about 500 ml, of de-ionized water further containing a non-ionic surfactant. The surfactant is typically present in concentration from about 0.05 to about 1.0 mg/ml, preferably about 0.23 mg/ml. Most preferred surfactant is PLURONIC® F127.

Typically, the washing step takes approximately 30 minutes. There may be one or several washing step repetitions. All excess non-precipitated collagen is removed during the extraction from the composite into the wash solution. Polymerizing of the collagen present in the secondary scaffold solution loaded within the primary scaffold pores results in formation of a stable double-structured composite, as defined above, comprising the primary scaffold and the secondary scaffold precipitated therewithin having shape memory.

Following the precipitation or gelling and washing, the composite is subjected to lyophilization and dehydrothermal treatment.

Stage 4—Dehydration of Composite Double-Structured Scaffold

The solid double-structured composite is then dehydrated using any method suitable for such dehydration. Typically, such dehydration will be freeze-drying or lyophilization. Freezing is typically carried out at temperature from about −10° C. to about −210° C., preferably from about −80° C., over a period of about 2 to about 60 minutes. The frozen composite is then lyophilized forming the Lyophilized Composite.

The gradual nature of the polymerization and slow process of water removal typically maintains the architectural elements of the secondary scaffold and achieves the proper orientation and diameter of the pores.

Step 6

Dehydration is achieved with freezing the solid double-structured composite by placing it on the metal shelf of a freezer and adjusting the temperature to from about −10° C. to about −210° C., preferably to about −60° C. to about −90°

C., and most preferably for about −80° C., for about 2 to about 60 minutes, preferably for about 20-45 minutes and most preferably for about 30 minutes.

Step 7

The frozen and dehydrated solid double-structured composite is then subjected to lyophilization. The frozen dehydrated composite is removed from the freezer and placed into a pre-cooled lyophilization chamber. Lyophilization typically occurs in about 15-21 hours, depending on the size and shape of the composite but is typically and preferably completed in about 18 hours.

Stage 5—Dehydrothermal Treatment

To further stabilize the composite and to achieve necessary stability, resistance to dissolution and sterility of the final product, the solid double-structured composite is subjected to dehydrothermal (DHT) treatment. DHT treatment achieves cross-linking of the collagen with the surfactant and at higher temperatures also sterilizes the DSTI.

Cross-linking step prevents dissolution of the secondary scaffold upon rehydration before or after implantation.

Step 8

This step is performed to sterilize and cross-link the double structured tissue implant.

The lyophilized double-structured composite is placed into a dry glass chamber or container and covered with the glass, aluminum foil or another suitable material resistant to higher temperatures. The container with the lyophilized double-structured composite is placed into the pre-heated dehydrothermal oven and subjected to a temperature in a range from about 70° C. to about 200° C., preferably from about 130° C. to about 150° C., and most preferably about 135° C., under vacuum, for about 30 minutes to about 7 days, preferably for about 5-7 hours and most preferably for about 6 hours.

Such treatment stabilizes the composite, makes it resistant to collagen dissolution upon wetting, provides for rapid wetting and assures none or minimal shrinkage or swelling upon wetting with a physiological solution or buffer, and sterilizes the double-structured tissue implant.

Stage 6—Packaging and Storage

The double-structured tissue implant fabricated by the process described above is then ready for a sterile packaging and storage. In this form, the DSTI has a long shelf-life.

Step 9

The double structured tissue implant is removed from the dehydrothermal oven and transferred aseptically into sterile environment, such as a Bio Safety Cabinet (BSC), where it is packaged under conditions assuring sterility. The double-structured tissue implant is then ready to be stored at room temperature until its use.

Stage 7—Delivery by Implantation

Packaged double-structured tissue implant is delivered or made available to a surgeon for implantation into a tissue defect.

Step 10

During surgery, surgeon determines an extent of the defect or lesion to be repaired, opens the packaged product, cuts the DSTI to size of the defects and places the cut-to-size piece into said defect. The implant may be wetted before the implantation and then placed into the defect or alternatively, it may be placed into the defect in a dry form and a suitable physiologically acceptable solution may be then added to wet the implant in situ.

Since the implant is very stable, and does not change its size or shape significantly by shrinking or swelling, the implant fits tightly into the defect or lesion. To assure that the implant stays within the defect or lesion, such defect or lesion is first coated with a suitable tissue adhesive, sealant or glue that keeps the implant in place. In alternative, the defect or lesion may be pretreated with microfracture where the tissue underlying the lesion or defect is microfractured with microchannels to permit the blood and nutrient supply into the lesion or defect, lining the defect or lesion but not the microfracture, with the adhesive, glue or sealant and placing the implant as described above. In both instances, the implant placed into the lesion or defect may optionally be covered with another layer of the adhesive, sealant or glue.

In some instances, cells, drugs or modulators may be loaded into the DSTI or attached to the second scaffold before implantation and wetting, during wetting following the implantation, or independently provided after the implantation.

Results obtained for three separate lots containing three rehydrated DSTIs per each lot, are seen in Table 2. The DSTI is rehydrated by placing a droplet of phosphate buffer saline (1.5× volume of PBS), on top of the DSTI and the rehydration time is measured as the time it takes for the DSTI to be completely hydrated.

TABLE 2

| Attribute | Number of Sample (n/lot) | Results | | |
|---|---|---|---|---|
| | | Lot #1 | Lot #2 | Lot #3 |
| Reydration Time (seconds) | 3 | <2 | <2 | <2 |
| Rehydrated pH | 3 | <2 | <2 | <2 |
| Rehydrated Osmolality (mOsm/kg) | 3 | 317 ± 6 | 356 ± 4 | 319 ± 1 |
| Size Variation at Hydration (%) | 3 | 99.8% ± 5.2± | 100.6% ± 10.0% | 99.7% ± 2.3% |
| Collagen Retention in PBS (%) | 3 | 99.4% ± 0.2% | 99.1% ± 0.1% | 99.2% ± 0.2% |

As seen in Table 2, results obtained in three different lots in three different studies are closely similar confirming the reproducibility of the process as well as consistency of the parameters observed after rehydration.

The rehydration time for each lot is less then 2 second evidencing a very fast wettability of the DSTI products.

The pH of the rehydrated DSTI products is between 7.7 and 7.8 in all lots.

Osmolality of the rehydrated DSTI products is between 317 and 356 mOsm/kg in all lots.

Variation in size of rehydrated DSTI products is negligible evidencing that there is no shrinkage or swelling upon hydration of DSTI Collagen retention within the rehydrated DSTI is above 99%, evidencing a great stability of the DSTI products.

III. Method of Use of Double-Structured Tissue Implant

Double-structured tissue implant of the invention is useful for treatment and repair of tissue defects of various tissues. Such treatment is achieved by implanting the DSTI into the defect in surgical setting.

A. Implantation of DSTI

In this regard, the use of DSTI, as described herein in FIGS. 9A-9E illustrates its implantation of DSTI into the articular cartilage lesion. However, the same or similar process would be used for implantation of the DSTI into defect of any other tissue.

Figure 9A:
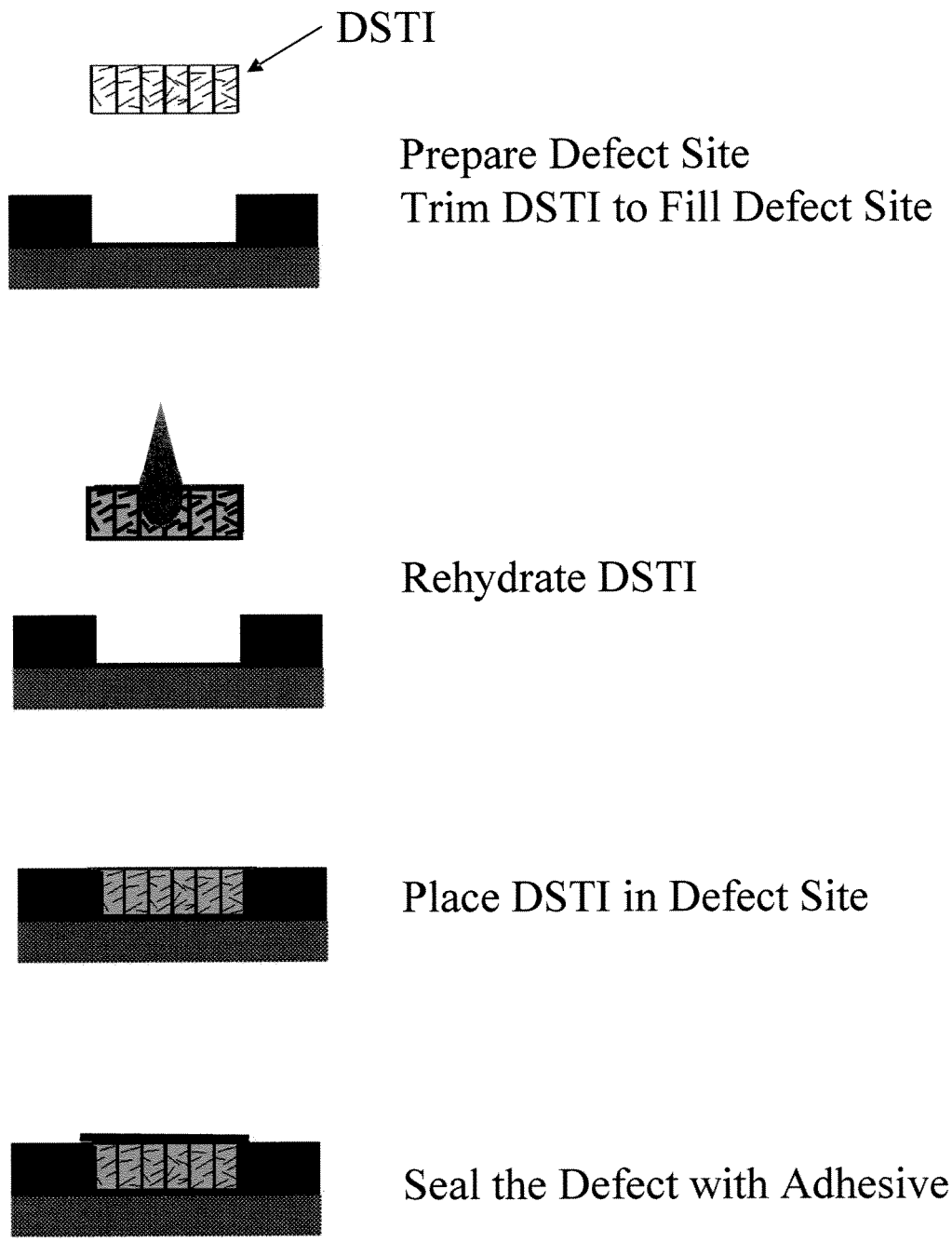
FIG. 9A is a schematic illustration of a basic method for implantation of the double-structured tissue implants (DSTI) into tissue defects or lesions.
Figure 9B:
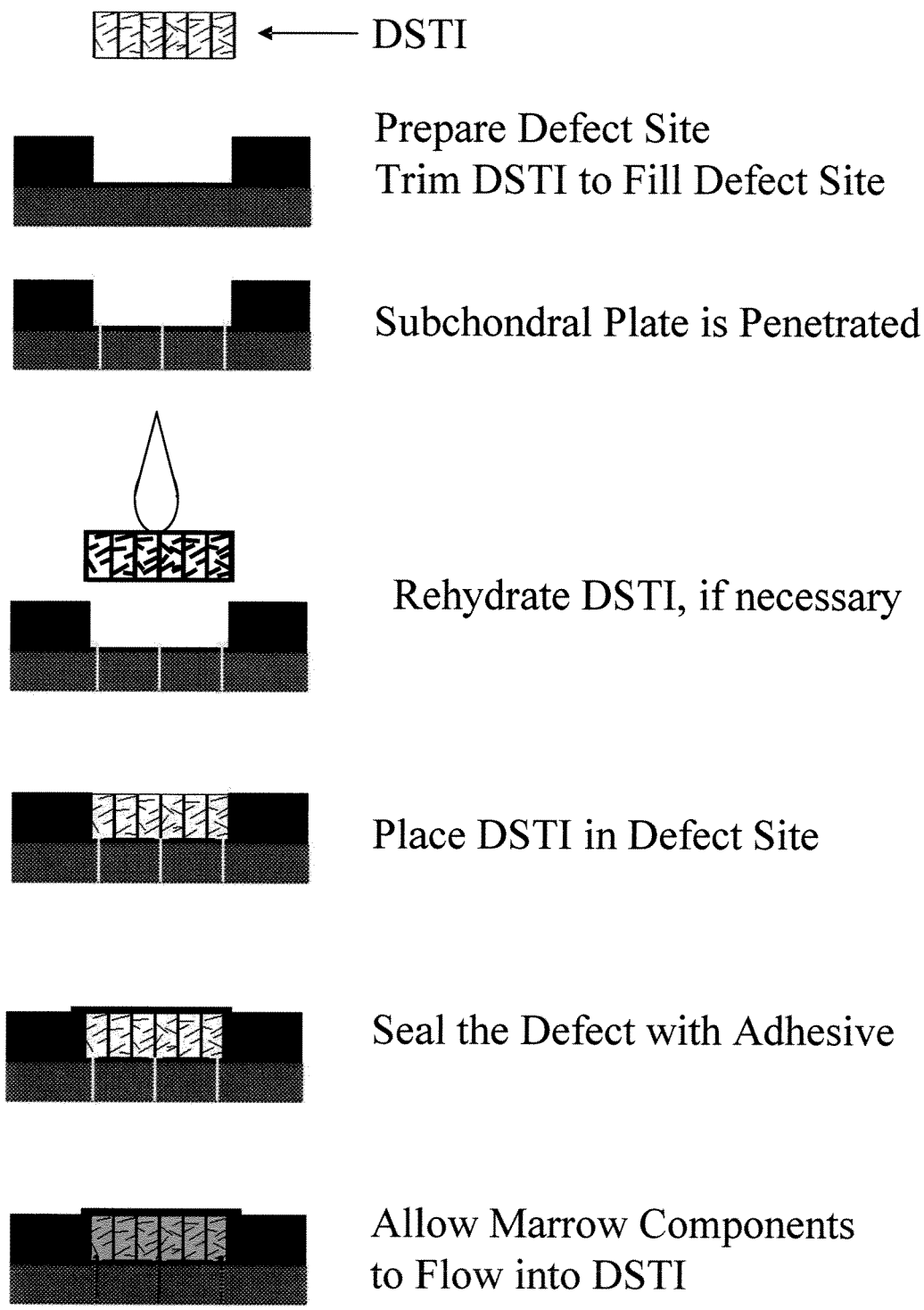
FIG. 9B shows the same method with microfracture pretreatment.

There are two basic methods suitable for implantation of DSTI into the tissue defect or lesion. The first method comprises implantation of the DSTI into the lesion without any special pretreatment of the lesion other than debriding and removing any undesirable debris from the defect or lesion before the DSTI deposition. The first method is illustrated in FIG. 9A. The second method comprises pretreatment of the defect or lesion with a microfracture technique. In such a case, a subchondral plate of the lesion is penetrated with microchannels connecting the bottom of the lesion or defect with underlying bone to permit the migration of cells, blood and nutrients into the deposited DSTI within the lesion or defect. The second method is illustrated in FIG. 9B.

Figure 9C:
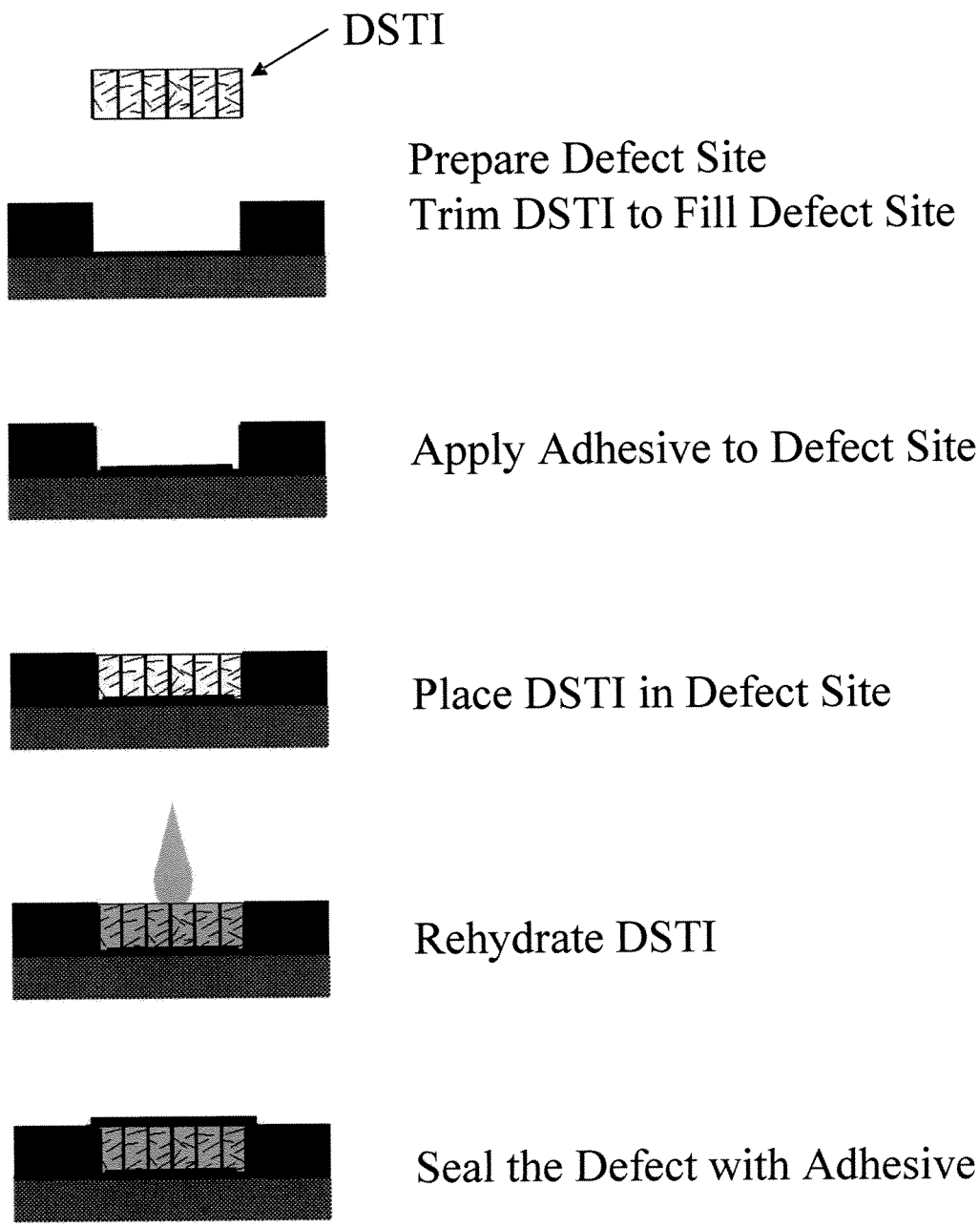
FIG. 9E illustrates a method for implantation of DSTI seeded with cultured cells activated with a hydrostatic pressure regimen.
Figure 9D:
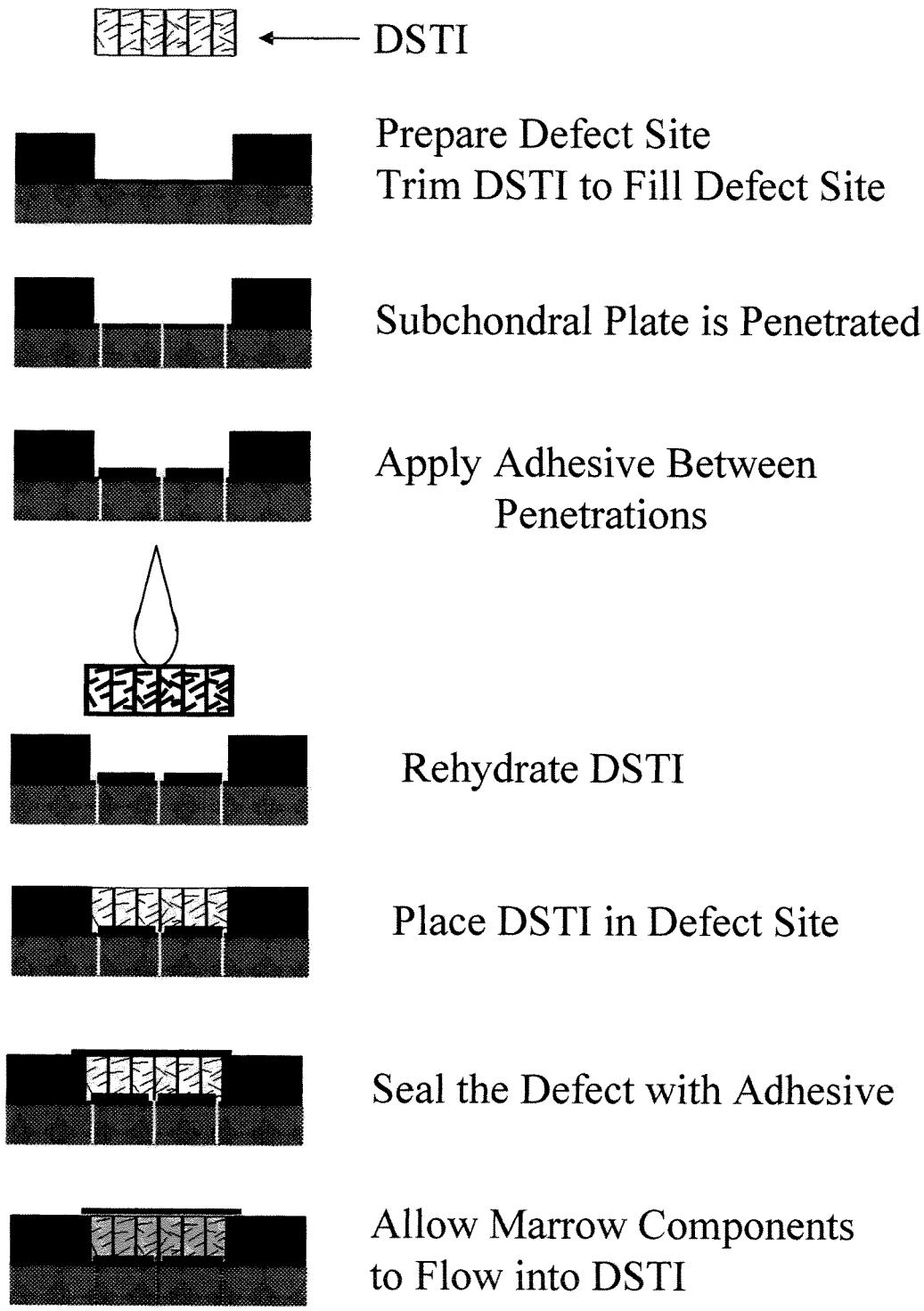

Additionally, the implantation method comprises two variations in attaching and sealing the DSTI within the defect or lesion. In the first and preferred mode, the DSTI is placed into the defect site and the tissue adhesive, preferably methylated collagen methylated collagen-polyethylene glycol, is placed over the defect containing the DSTI. The second variation of the implantation method comprises, additionally, a step of placing a second adhesive at the bottom of the lesion or defect before the placement of DSTI. This variation is seen in FIGS. 9C and 9D. Although it is preferred to use only one adhesive over the implanted DSTI, in some instances, the use of the second adhesive placed at the bottom of the lesion is warranted. For example, when the DSTI is prepared as an implant seeded with in vitro cultured and/or activated cells when the implant itself is already filled with cells and extracellular matrix, as seen in FIG. 9E, rather than being rehydrated with solution of cells or bone marrow, the deposition of the bottom adhesive may be required. Adhesives suitable for sealing the defect and securing it may be the same or different and are, typically, compounds polymerizable within short time from about 30 seconds to about 4 minutes with or without use of a curing means.

The cells that may be seeded into the DSTI in vitro may be cultured and activated using an intermittent hydrostatic pressure, as described by inventors in copending U.S. application Ser. Nos. 10/626,459, 10/104,677, 10/625,822, 10/625,245 and 10/882,581, hereby incorporated by reference in their entirety. Intermittently applied hydrostatic pressure has been shown to support development of a new hyaline cartilage in articular joints.

FIG. 9A is a schematic illustration of a basic method for implantation of the double-structured tissue implants (DSTI) into tissue defects or lesions in an operating room setting. The first step in the implantation method comprises preparing a defect site for implantation of DSTI. Such preparation comprises debriding the lesion or defect of tissue debris, blood, blood clots, etc. When the defect is prepared for implantation, surgeon cuts and trims the DSTI to a size and shape of the defect. DSTI is supplied to surgeon in dry or wet form in a sterile packaging such as shown in FIG. 1B. After trimming the DSTI into the appropriate size and shape, the DSTI is rehydrated, typically with saline, collagen containing solution or another physiologically acceptable solution, Such solution may be added before the DSTI is placed into the defect or, preferably, after it is placed into the defect. The added solution may be without any additional components or it may contain cells, pharmaceutical agents, growth hormones, modulators, blood thinners or buffers. The DSTI placed into the defect or lesion is then sealed using a biocompatible and biodegradable polymeric tissue adhesive, (preferably methylated collagen polyethylene glycol).

FIG. 9B shows essentially the same method as described in FIG. 9A with added step for microfracture pretreatment. The defect site is prepared and an initially oversized double-structured tissue implant (DSTI) is cut and trimmed to match the size and shape of the defect. The subchondral plate of the defect site is penetrated using the microfracture technique. The precut DSTI is rehydrated with saline, collagen containing solution or other physiologically acceptable solution and placed into the defect. Alternatively, the dehydrated DSTI is implanted and rehydrated in situ. The DSTI may be rehydrated with a physiologically acceptable solution optionally containing cells, cell progenitors or agents that stimulate healing. The defect site is sealed with a tissue adhesive applied over the implant.

FIG. 9C is a schematic illustration of a variation of a basic method for implantation of the double-structured tissue implants (DSTI) into tissue defects or lesions during surgery. In this method, the adhesive is added first to the bottom of the defect and cured or left non-cured, depending on the DSTI. Typically, the first adhesive is deposited and should be left uncovered until it is completely or at least it is partially polymerized. The first step in the implantation method comprises preparing defect site for implantation of DSTI. Such preparation comprises debriding the lesion and coating said defect with a biocompatible biodegradable polymeric adhesive. When the defect is prepared for implantation, surgeon cuts and trims the DSTI to a size and shape of the defect. In this instance, the DSTI is typically pre-seeded with cells that have been previously cultured and activated using methods referred to above. The pre-seeded DSTI is supplied to a surgeon in dry or wet form in a sterile packaging similar to that shown in FIG. 1B. After trimming the DSTI into the appropriate size and shape, the DSTI is rehydrated, typically with saline or another physiologically acceptable solution, such solution may be added before the DSTI is placed into the defect or, preferably, after it is placed into the defect. The added solution may contain pharmaceutical agents, growth hormones or modulators. The DSTI placed into the defect or lesion is then sealed using a biodegradable tissue adhesive, preferably methylated collagen polyethylene glycol. The tissue adhesive used to coat the bottom of the defect may be same or different adhesive used to seal the implanted defect.

For a variation of the basic microfracture method seen in FIG. 9B, the microfractured defect seen in FIG. 9D, is treated with the bottom adhesive similarly to the method described in FIG. 9C, except that the bottom adhesive is applied at the bottom of the defect between microfracture penetrations.

FIG. 9E illustrates a method for implantation of DSTI seeded with cultured cells activated with a hydrostatic pressure regimen. The method is similar to that seen in FIG. 9C.

B. Tissue Adhesives and Sealants

The double-structured tissue implant is implanted into a tissue defect or cartilage lesion covered with a biocompatible adhesive, tissue sealant or glue. Typically, the sealant is deposited at and covers the bottom of the defect or lesion and may also be used to cover the implant after implantation.

Generally, the tissue sealant or adhesive useful for the purposes of this application has adhesive, or peel strengths at least 10 N/m and preferably 100 N/cm; has tensile strength in the range of 0.2 MPa to 3 MPa, but preferably 0.8 to 1.0 MPa. In so-called Alap shear" bonding tests, values of 0.5 up to 4-6 N/cm2 are characteristic of strong biological adhesives.

Such properties can be achieved by a variety of materials, both natural and synthetic. Examples of suitable sealant include gelatin and di-aldehyde starch described in PCT WO 97/29715, 4-armed pentaerythritol tetra-thiol and polyethylene glycol diacrylate described in PCT WO 00/44808, photo-polymerizable polyethylene glycol-co-poly(a-hydroxy acid) diacrylate macromers described in U.S. Pat. No. 5,410,016, periodate-oxidized gelatin described in U.S. Pat. No. 5,618,551, serum albumin and di-functional polyethylene glycol derivatized with maleimidyl, succinimidyl, phthalimidyl and related active groups described in PCT WO 96/03159.

Sealants and adhesives suitable for purposes of this invention include sealants prepared from gelatin and dialdehyde starch triggered by mixing aqueous solutions of gelatin and dialdehyde starch which spontaneously react and/or those made from a copolymer of polyethylene glycol and polylactide, polyglycolide, polyhydroxybutyrates or polymers of aromatic organic amino acids and sometimes further containing acrylate side chains, gelled by light, in the presence of some activating molecules.

Another type of the suitable sealant is 4-armed polyethylene glycol derivatized with succinimidyl ester and thiol plus methylated collagen in two-part polymer compositions that rapidly form a matrix where at least one of the compounds is polymeric, such as polyamino acid, polysaccharide, polyalkylene oxide or polyethylene glycol and two parts are linked through a covalent bond, for example a cross-linked derivatized PEG with methylated collagen, such as methylated collagen polyethylene glycol.

Preferable sealants are 4-armed tetra-succinimidyl ester PEG, tetra-thiol derivatized PEG and PEG derivatized with methylated collagen (known as CT3), commercially available from Cohesion Inc., Palo Alto, Calif. and described in U.S. Pat. Nos. 6,312,725B1 and 6,624,245B2 and in J. Biomed. Mater. Res., 58:545-555 (2001), J. Biomed. Mater. Res., 58:308-312 (2001) and The American Surgeon, 68:553-562 (2002), all hereby incorporated by reference.

Sealants and adhesives described in copending U.S. application Ser. No. 10/921,389 filed Aug. 18, 2004 and Ser. No. 11/525,782 filed Dec. 22, 2006, are hereby incorporated by reference.

C. Activation of Cells within DSTI

Activation of the cells prior to their seeding into a DSTI comprises steps:

a. isolation and/or collection of cells, such as chondrocytes or stem cells from a donor tissue; with or without expansion of the number of cells.

b. seeding the cells in a DSTI;

c. subjecting the seeded DSTI to a static, constant or cyclic hydrostatic pressure above atmospheric pressure (about 0.5-3.0 MPa at 0.5 Hz) with medium perfusion rate of 5 μl/min for several (5-10) days; and d. subjecting the seeded DSTI to a resting period for ten to fourteen days at constant (atmospheric) pressure.

Seeded DSTI obtained by the above-outlined conditions and method show that a combination of hydrostatic pressure and static pressure has advantage over conventional culture methods by resulting in higher cell proliferation and extracellular matrix accumulation within DSTI. Use of DSTI maintains uniform cell distribution within the primary and secondary scaffolds that also provides support for newly synthesized extracellular matrix. Obtained seeded DSTI is easy to handle and manipulate and can be easily stored and safely implanted in a surgical setting.

Combination of a period of cyclic hydrostatic pressure under low medium perfusion rate followed up with a period of static culture (resting period) results in increased cell proliferation, increased production of Type II collagen, increased DNA content and increased S-GAG accumulation.

Increased cell proliferation shows that the harvested inactive non-dividing cells, particularly chondrocytes, have been activated into active, dividing and multiplying chondrocytes. Increased level of DNA shows genetic activation of inactive chondrocytes. Increased production of Type II collagen and S-GAG shows that production of the extracellular matrix has been activated using the method for activation described above.

Although the optimized conditions described above is preferred, it is to be understood that these conditions may be advantageously changed using variations of ranges of cyclic hydrostatic pressure, flow rate, duration of the pressure and resting period, particularly when applied to different cells or tissue. All variations of all conditions and combinations thereof are intended to be within the scope of this invention.

D. Use of DSTI for Treatment of Chondral Defects

One example of utility of the DSTI is its use for treatment of chondral defects.

To be successful for treatment of articular cartilage, the DSTI must provide conditions allowing the chondrocytes or mesenchymal stem cells seeded therein to be able to form, generate or induce the generation of the new extracellular matrix. In this regard, the DSTI pore structure must allow cells to migrate into the pores and function similarly to their normal function in the healthy tissue. The extracellular matrix formed by the cells seeded within the DSTI then provides means for growing a new hyaline or hyaline-like cartilage for treatment, replacement or regeneration of the damaged or injured articular cartilage. Such treatment is currently difficult because of the unique properties of the articular cartilage that is not the same as and does not behave as other soft tissues.

E. Use of DSTI for Treatment of Other Conditions

In addition to cartilage repair, a number of other chronic conditions represent instances where the implantation of the double structured scaffold can provide a clinically important bridge for tissue repair.

For example, genitourinary tissues have been fabricated from a variety of materials. The DSTI once placed at the site of tissue damage will provide a support for development of new tissues occurs in accordance with predefined configuration. In these applications, similar to cartilage, the DSTI must resist the dynamic forces generated by the surrounding muscle and connective tissues and maintaining its structure during a necessary period of cellular infiltration and tissue formation.

The rapidity by which tissue differentiation and structural integrity are established is subject to modulation through the use specific signaling factors localized within the primary and secondary collagenous composite. Although the limits by which, for example, new muscle formation can be derived from progenitor cells, suggests that localization of the mesenchymal cells to the site of damage in response to homing molecules, such as chemokines and cell receptor ligands, may be used to accelerate repair of muscle, either cardiac or skeletal. DSTI may be used to deliver these cells or modulators to the site of damage.

Finally, wound healing applications have remained a primary goal in the use of tissue implants for cell-based tissue repair. Treatment of acute and chronic wounds is dependent on a multi-faceted transition by which progenitor cells encounter soluble mediators, formed blood elements, extracellular matrix macromolecules and parenchymal cells that then serve to reestablish a body surface barrier through epithelialization. In this instance either the double-structured scaffold or the stand alone secondary scaffold implant may provide a novice stromal layer into which blood vessels and progenitor cells can migrate. From this migration, the progenitor cells may then undergo differentiation into the fibroblast stromal cell and generate or recruit epithelial cells to support reestablishment of dermal and epidermal layers at the time of wound closure.

IV. Basic Requirements for DSTI

The collagen-based primary and secondary scaffolds of the DSTI are essential components of the DSTI and are responsible for capability of DSTI to initiate the repair and induction of repair of tissue defects.

The first requirement is that the scaffolds are prepared from the biocompatible and preferably biodegradable materials that are the same or similar to those observed in the tissues to be repaired, hence the instant DSTI are prepared from collagen or collagen-like materials.

The second requirement is that the scaffolds have a spatial organization and orientation similar to that of the tissue to be repaired. The porous structure of both primary and secondary scaffold provides such organization. The third requirement is that the scaffold has a pore density permitting the seeding of the cells into said scaffolds in numbers needed for initiation of a tissue recovery or formation of new tissue in vivo. The substantially homogenous pore size and distribution within the DSTIs allows the cell seeding and assures cell viability.

The fourth requirement is that the scaffolds have sufficient number of pores for the number of cells needed for initiation of the tissue recovery and repair. The spatial organization of both scaffolds has optimized number of pores.

The fifth requirement is that the pores have substantially the same size and that such size is substantially the same from the top apical to the bottom basal surface of the pores, said pores being organized substantially vertically from the top to the bottom. The primary scaffold has such organization.

The sixth requirement is stability of the DSTI. The double-structured organization of the DSTI provides such stability during wetting, reconstitution, and resistance to dissolution and to shrinkage or swelling.

The seventh requirement is that DSTI provides support and conditions for cell migration from the surrounding tissue, for integration of seeded cells into the surrounding tissue and generally that assures the cell viability. The DSTI provides such conditions and the cells seeded within DSTI have almost 100% viability.

Example 1

Preparation of the Primary Scaffold

This example describes one exemplary method for preparation of the collagen-based primary scaffold suitable as a structural support for preparation of the DSTI. Type I collagen is dissolved in a weak hydrochloric acid solution at pH 3.0 with the collagen concentration and osmolality of the solution adjusted to about 3.5 mg/ml and 20 mOsm/kg, respectively. The solution (70 ml) is poured into a 100 ml Petri dish and the Petri dish containing the collagen solution is centrifuged at 400×g for 30 minutes to remove air bubbles. Neutralization and subsequent precipitation or gelling is carried out in a 7 liter chamber containing 10 ml of 15% ammonia solution over a 45 minutes period. The precipitated collagen is then washed in a large excess of de-ionized water. The water is changed as many times as needed over next 3 days to remove formed salts and excess ammonia.

The solution is then subjected to unidirectional freezing over a period of about 4 hours. The Petri dish is placed on a stainless steel disc which is partially submerged in a cooling bath. The temperature of the cooling bath is increased from 0° C. to −18° C. at a rate of 0.1° C./minute. The frozen water is removed by lyophilization over a period of about 3 days. The lyophilized primary scaffold is then dehydrothermally (DHT) treated at 135° C. for about 18 hours before being precut into slices of an appropriate thickness.

The organization of the newly synthesized cartilage specific matrix within the porous type I collagen is visualized and quantified using histological and image analysis methods.

Example 2

Preparation of a Basic Solution for a Secondary Scaffold

This example describes preparation of the Basic Solution used for formation of the secondary scaffold. The Basic Solution comprises a soluble collagen in admixture with a PLURONIC® surfactant. The Basic Solution is incorporated into the primary scaffold and processes into the double scaffold tissue implant or processed as a stand alone implant.

Solution for the secondary scaffold is prepared by mixing PLURONIC® F127 (2.32 mg, 0.29 mg/ml), obtained commercially from BASF, Germany, with 8 ml of a solution containing 2.9 mg/ml bovine type I collagen dissolved in hydrochloric acid (pH 2.0) at room temperature. The resulting solution is neutralized with 1 ml of 10× Dulbecco=s phosphate buffered saline (DPBS) and 1 ml of 0.1M NaOH to the final pH of 7.4.

In the alternative, the neutralization is achieved by ammonia aqueous solution or ammonia vapor in concentration sufficient to neutralize acid within the collagen solution.

Example 3

Preparation of the Secondary Scaffold as Stand Alone Unit

This example illustrates preparation of the secondary scaffold as a stand alone implant or stand alone unit. For preparation of the stand alone secondary scaffold, the Basic Solution prepared in Example 3 is subjected to precipitation or gelling followed by dehydrothermal treatment.

The Basic Solution (2 ml) comprising collagen and PLURONIC® surfactant is placed in a small glass beaker and the beaker is placed into a chamber (approximately 9 liters) charged with 1% ammonia solution. The Basic Solution is allowed to precipitate in the chamber over a period of 15 minutes. The gelled or precipitated collagen is then washed in 500 ml of deionized water over a period of 30 minutes. The washing step is repeated three times. The washed gel or precipitate is placed on metal shelf of a freezer at −80° C. over a period of 30 minutes. The frozen gel or precipitate is removed from the freezer and lyophilized. Lyophilization is performed over a period of 10 hours. The lyophilized construct is then dehydrothermally treated at 135° C. under vacuum for a period of 6 hours to form the secondary scaffold alone.

Example 4

Preparation of the Double-Structured Tissue Implant

This example describes preparation of the double-structured tissue implant (DSTI). The preparation of DSTI includes incorporation of a Basic Solution for formation of a secondary scaffold within the primary scaffold and its further processing into DSTI.

4.9 ml (1.3× volume of the primary scaffold) of the neutralized basic collagen/PLURONIC® solution prepared in Example 2, is placed in a dish and a primary scaffold, prepared in Example 1, precut into a square having 50×50×1.5 mm dimensions is then placed into the neutralized Basic Solution for the secondary scaffold. The basic neutralized solution is absorbed into the primary scaffold by wicking or soaking.

The primary scaffold containing the neutralized solution is then placed in a 37° C. incubator over a period of 50 minutes to precipitate or gel the neutralized collagen solution. The composite consisting of the primary scaffold with the gelled or precipitated neutralized solution within is then washed in 500 ml of deionized water over a period of 30 minutes. The washed composite is placed on metal shelf of a freezer at a temperature −801 C over a period of 30 minutes. The frozen composite is removed from the freezer and lyophilized.

Lyophilization is performed over a period of 18 hours. The lyophilized composite is then dehydrothermally treated at 1351 C under vacuum for a period of 6 hours to form the double-structured tissue implant (DSTI).

The DSTI is removed from the dehydrothermal oven and transferred aseptically into a Bio Safety Cabinet (BSC) where it is packaged.

Example 5

Determination of Retention of Collagen within DSTI

This example describes a procedure used for determination of the stability of the double-structured tissue implant in vitro.

Three lots of DSTIs are prepared as described in Example 4 and cut to a size of 1.5×1.5×0.15 cm. Cut DSTIs are placed in 35 mm Petri dishes, rehydrated with 450 cl of phosphate buffered saline and additional 2 ml of phosphate buffered saline are added to each Petri dish containing the DSTI. The analysis for each lot consists of three replicates for a total of 9 samples for the three lots.

Dishes containing individual DSTIs are placed in the incubator for the duration of testing. In the predetermined intervals of zero hour, 1 hour, 3 days, 7 days and 14 days, 1 ml aliquot of the phosphate buffered saline is removed from each plate. Each removed 1 ml is replaced with 1 ml of a fresh phosphate buffer saline. The removed aliquots are subjected to a colorimetric protein assay for quantification of total collagen released into the saline.

Cumulative collagen retention curves are generated by subtraction of the amount of collagen released into the solution from the theoretical collagen load estimated at 0.777 mg of collagen/DSTI sample. Results are seen in FIG. 6.

Example 6

Determination of Change of Size and Shape of DSTI Following Rehydration

This example describes the retention of size and shape of double-structured tissue implant in a phosphate buffered saline solution over time.

The DSTI samples obtained in Example 5 are photographed at the designated intervals and the images generated are measured by ImageJ, publicly available Java-based image processing program developed at the NIH. The photograph of each sample at each time point is imported into Image and the region of interest (DSTI area) is manually defined. The area was measured and the percent change is determined by dividing the areas at each time point by the rehydrated DSTI at time 0 and multiplying by 100. Results are seen in FIG. 7.

Example 7

Studies of Biocompatibility

This example describes procedures used to determine cell biocompatibility with the primary scaffold and with the DSTI.

The primary scaffold and DSTIs are prepared in three lots as described in Examples 1 and 4. The chondrocytes or other cells are loaded into the three samples of primary scaffolds and into the three lots of three samples each of DSTIs. Time intervals for biochemical, image and cell viability determination is set to Day 0 (24 hours) and Day 21 (21 days) of incubation in the culture medium.

TABLE 3

Chondrocyte Compatibility Experimental Groups

| | | Time | Sample Numbers | | |
|---|---|---|---|---|---|
| Group | Description | point | Biochemistry | Images | Viability |
| A | DSTI #1 | Day 0 | 3 | 2 | 3 |
| B | DSTI #1 | Day 21 | 3 | 2 | 3 |
| C | DSTI #2 | Day 0 | 3 | 2 | 3 |
| D | DSTI #2 | Day 21 | 3 | 2 | 3 |
| E | DSTI #3 | Day 0 | 3 | 2 | 3 |
| F | DSTI #3 | Day 21 | 3 | 2 | 3 |
| G | Primary Scaffold | Day 0 | 3 | 2 | 3 |
| H | Primary Scaffold | Day 21 | 3 | 2 | 3 |

DSTI-5 mm disks are cut from each lot of sheets.

Primary scaffold 5 mm disks are cut from primary scaffold.

The disks of the primary scaffold are loaded with the chondrocytes dissolved in a collagen solution at a cell concentration of 5×10⁶ cells/ml. The primary scaffold does not contain the surfactant and is not subjected to lyophilization or to a dehydrothermal treatment.

Both the primary scaffold and DSTI disks (total 24) are placed in 24 well plates. Chondrocytes are seeded into the disks by the addition of 20 µl of 3D cell culture medium (DMEM/F-12+10% FBS+1% ITS) at a cell concentration of 5×10⁶ cells/ml. The disks loaded with cells are placed in the incubator for 1 hour at 37° C. and in 5% CO2. Then 400 µl of medium is added and the plates are placed in the low oxygen incubator overnight. At 24 hours (Day 0), one set of samples from each lot is removed from culture. The remaining disks loaded with chondrocytes are transferred to 12 well plates with 2 ml of 3D culture medium and are maintained in culture at 37° C., 5% CO2, 2% O2 for three weeks with medium changes once a week.

The primary scaffold disks are processed in the same way as DSTI disks.

Evaluations include assessment of chondrocyte growth, viability and phenotypic S-GAG expression in both the primary scaffold and DSTIs. Results are seen in FIG. 4B, and FIG. 5 for DSTI images, FIG. 8 for S-GAG and DNA production and in Table 1 for cell viability.

Example 8

Production of S-GAG/DNA

This example describes conditions used for evaluation of production of S-GAG and DNA by seeded chondrocytes.

DSTI and primary scaffold disks are prepared as described in Examples 1 and 4 and seeded with 200,000 chondrocytes in 20 µl of 3D culture medium by absorption at 37 CC for 1 hour. 400 µl of medium is added and incubated overnight. Disks are removed for analysis at predetermined intervals.

At termination, the disks are placed in papain digest solution and incubated at 60° C. overnight. An aliquot of the digest from each disk is taken to measure S-GAG by the dimethylmethylene blue assay. An aliquot from each disk is taken for measurement of DNA by the Hoechst dye method. Results are shown in FIG. 8.

Example 9

Determination of Viability of Chondrocytes

This example describes procedure used for determination of viability of chondrocytes seeded in the DSTIs or in the primary or secondary scaffolds.

DSTI, primary scaffold or secondary scaffold disks are seeded with approximately 200,000 chondrocytes dissolved in the 20 µl of 3D culture medium by absorption and incubated at 37 CC for 31 hours. 400 µl of medium is added and incubation is continued overnight.

Cell loaded disks are removed for analysis and 2 ml of medium is added to remaining disks for continued incubation for 21 days.

At day 21, the chondrocyte-loaded DSTIs and the primary and secondary scaffolds disks are placed in 1.5 ml microcentrifuge tubes and further incubated overnight in 0.15% collagenase. The digest is centrifuged at 2000 rpm for 5 minutes and the supernatant aspirated. An aliquot of culture medium (0.1 ml) is added to the cell pellets and an aliquot taken for counting. Cell viability and total cell count is determined using trypan blue. Results are shown in Table 1.

What is claimed:

1. A method for treating a tissue defect comprising:
   a. preparing a double-structured tissue implant comprising a three-dimensional primary scaffold;
   b. preparing said tissue defect for implantation;
   c. precutting said double-structured tissue implant;
   d. coating said defect with a first tissue adhesive;
   e. implanting said double-structured tissue implant into said defect, wherein said implant is rehydrated with a physiologically acceptable solution or buffer before or after implantation; and
   f. covering said implant with a second tissue adhesive;

wherein said three-dimensional primary scaffold comprises a plurality of pores, wherein said plurality of pores comprises a secondary scaffold comprising lyophilized and dehydrothermally treated collagen and a surfactant, and wherein said secondary scaffold forms a fibrous and cross-linked collagen network within said plurality of pores.

2. The method of claim 1, wherein said primary scaffold defines a top surface and a bottom surface of said implant.

3. The method of claim 1, wherein the collagen has been lyophilized at a temperature of about −10° C. to about −210° C. over a period of about 2 to about 60 minutes and dehydrothermally treated at a temperature of about 70° C. to about 200° C. for about 30 minutes to about 7 days.

4. The method of claim 1, wherein the pores have a diameter of about 300±100 pm.

5. The method of claim 4, wherein the sizes and diameters of the pores on both a top surface and a bottom surface are substantially the same.

6. The method of claim 5, wherein the pores are vertically oriented.

7. The method of claim 1, wherein the secondary scaffold comprises Type I collagen.

8. The method of claim 1, wherein the surfactant is a derivatized polyethylene glycol.

9. The method of claim 1, wherein the implant further comprises a morphogenetic growth factor.

10. The method of claim 1, wherein the implant further comprises a modulator.

11. The method of claim 1, wherein the implant further comprises a pharmaceutical agent, a growth factor, a growth hormone, a mediator, an enzyme promoting cell incorporation, an enzyme promoting cell proliferation, an enzyme promoting cell division, a pharmaceutically acceptable excipient, an additive, a buffer, a transforming growth factor, an insulin-like growth factor 1, a platelet-derived growth factor, a repulsive guidance molecule, or a bone morphogenetic protein (BMP).

* * * * *